United States Patent
Huelskamp et al.

(10) Patent No.: US 10,065,041 B2
(45) Date of Patent: Sep. 4, 2018

(54) DEVICES AND METHODS FOR ADJUSTING PACING RATES IN AN IMPLANTABLE MEDICAL DEVICE

(71) Applicant: Cardiac Pacemakers, Inc., St. Paul, MN (US)

(72) Inventors: Paul Huelskamp, St. Paul, MN (US); Michael J. Kane, Roseville, MN (US); Douglas J. Gifford, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/288,500

(22) Filed: Oct. 7, 2016

(65) Prior Publication Data
US 2017/0100594 A1    Apr. 13, 2017

Related U.S. Application Data

(60) Provisional application No. 62/239,025, filed on Oct. 8, 2015.

(51) Int. Cl.
*A61N 1/365* (2006.01)
*A61N 1/362* (2006.01)
*A61N 1/375* (2006.01)

(52) U.S. Cl.
CPC ........ *A61N 1/36521* (2013.01); *A61N 1/3621* (2013.01); *A61N 1/36542* (2013.01); *A61N 1/3756* (2013.01)

(58) Field of Classification Search
CPC .............. A61N 1/36521; A61N 1/3621; A61N 1/36542; A61N 1/3756
See application file for complete search history.

(56) References Cited

U.S. PATENT DOCUMENTS

| 3,835,864 A | 9/1974 | Rasor et al. |
| 3,943,936 A | 3/1976 | Rasor et al. |

(Continued)

FOREIGN PATENT DOCUMENTS

| AU | 2008279789 B2 | 10/2011 |
| AU | 2008329620 B2 | 5/2014 |

(Continued)

OTHER PUBLICATIONS

US 8,886,318, 11/2014, Jacobson et al. (withdrawn)

(Continued)

*Primary Examiner* — Catherine Voorhees
(74) *Attorney, Agent, or Firm* — Seager, Tufte & Wickhem LLP

(57) ABSTRACT

Systems, devices, and methods are disclosed for limiting the duration of elevated pacing rates in an implantable medical device. An illustrative device may include a housing, a plurality of electrodes connected to the housing, and a controller within the housing and connected to the electrodes. The controller may deliver pacing pulses to the electrodes at a base pacing rate, detect a measure of elevated metabolic demand which may vary over time, deliver pacing pulses at an elevated pacing rate based on the measure of elevated metabolic demand. The controller may change a heart stress tracking value (HSTV) when the pacing rate is elevated and may be changed faster during times of relatively higher elevated pacing rates than times of relatively lower elevated pacing rates. The elevated pacing rate may be reduced back toward the base pacing rate after the HSTV crossed a predetermined heart stress threshold.

20 Claims, 13 Drawing Sheets

(56) References Cited

U.S. PATENT DOCUMENTS

| | | | |
|---|---|---|---|
| 4,142,530 A | 3/1979 | Wittkampf | |
| 4,151,513 A | 4/1979 | Menken et al. | |
| 4,157,720 A | 6/1979 | Greatbatch | |
| RE30,366 E | 8/1980 | Rasor et al. | |
| 4,243,045 A | 1/1981 | Maas | |
| 4,250,884 A | 2/1981 | Hartlaub et al. | |
| 4,256,115 A | 3/1981 | Bilitch | |
| 4,263,919 A | 4/1981 | Levin | |
| 4,310,000 A | 1/1982 | Lindemans | |
| 4,312,354 A | 1/1982 | Walters | |
| 4,323,081 A | 4/1982 | Wiebusch | |
| 4,357,946 A | 11/1982 | Dutcher et al. | |
| 4,365,639 A | 12/1982 | Goldreyer | |
| 4,440,173 A | 4/1984 | Hudziak et al. | |
| 4,476,868 A | 10/1984 | Thompson | |
| 4,522,208 A | 6/1985 | Buffet | |
| 4,537,200 A | 8/1985 | Widrow | |
| 4,556,063 A | 12/1985 | Thompson et al. | |
| 4,562,841 A | 1/1986 | Brockway et al. | |
| 4,593,702 A | 6/1986 | Kepski et al. | |
| 4,593,955 A | 6/1986 | Leiber | |
| 4,630,611 A | 12/1986 | King | |
| 4,635,639 A | 1/1987 | Hakala et al. | |
| 4,674,508 A | 6/1987 | DeCote | |
| 4,712,554 A | 12/1987 | Garson | |
| 4,729,376 A | 3/1988 | DeCote | |
| 4,754,753 A | 7/1988 | King | |
| 4,759,366 A | 7/1988 | Callaghan | |
| 4,776,338 A | 10/1988 | Lekholm et al. | |
| 4,787,389 A | 11/1988 | Tarjan | |
| 4,793,353 A | 12/1988 | Borkan | |
| 4,819,662 A | 4/1989 | Heil et al. | |
| 4,858,610 A | 8/1989 | Callaghan et al. | |
| 4,886,064 A | 12/1989 | Strandberg | |
| 4,887,609 A | 12/1989 | Cole, Jr. | |
| 4,928,688 A | 5/1990 | Mower | |
| 4,967,746 A | 11/1990 | Vandegriff | |
| 4,969,467 A * | 11/1990 | Callaghan | A61N 1/36507 607/13 |
| 4,987,897 A | 1/1991 | Funke | |
| 4,989,602 A | 2/1991 | Sholder et al. | |
| 5,012,806 A | 5/1991 | De Bellis | |
| 5,036,849 A | 8/1991 | Hauck et al. | |
| 5,040,534 A | 8/1991 | Mann et al. | |
| 5,058,581 A | 10/1991 | Silvian | |
| 5,078,134 A | 1/1992 | Heilman et al. | |
| 5,109,845 A | 5/1992 | Yuuchi et al. | |
| 5,113,859 A | 5/1992 | Funke | |
| 5,117,824 A | 6/1992 | Keimel et al. | |
| 5,127,401 A | 7/1992 | Grevious et al. | |
| 5,133,353 A | 7/1992 | Hauser | |
| 5,144,950 A | 9/1992 | Stoop et al. | |
| 5,170,784 A | 12/1992 | Ramon et al. | |
| 5,179,945 A | 1/1993 | Van Hofwegen et al. | |
| 5,193,539 A | 3/1993 | Schulman et al. | |
| 5,193,540 A | 3/1993 | Schulman et al. | |
| 5,241,961 A | 9/1993 | Henry | |
| 5,243,977 A | 9/1993 | Trabucco et al. | |
| 5,259,387 A | 11/1993 | dePinto | |
| 5,269,326 A | 12/1993 | Verrier | |
| 5,284,136 A | 2/1994 | Hauck et al. | |
| 5,300,107 A | 4/1994 | Stokes et al. | |
| 5,301,677 A | 4/1994 | Hsung | |
| 5,305,760 A | 4/1994 | McKown et al. | |
| 5,312,439 A | 5/1994 | Loeb | |
| 5,313,953 A | 5/1994 | Yomtov et al. | |
| 5,314,459 A | 5/1994 | Swanson et al. | |
| 5,318,597 A | 6/1994 | Hauck et al. | |
| 5,324,316 A | 6/1994 | Schulman et al. | |
| 5,331,966 A | 7/1994 | Bennett et al. | |
| 5,334,222 A | 8/1994 | Salo et al. | |
| 5,342,408 A | 8/1994 | Decoriolis et al. | |
| 5,370,667 A | 12/1994 | Alt | |
| 5,372,606 A | 12/1994 | Lang et al. | |
| 5,376,106 A | 12/1994 | Stahmann et al. | |
| 5,383,915 A | 1/1995 | Adams | |
| 5,388,578 A | 2/1995 | Yomtov et al. | |
| 5,404,877 A | 4/1995 | Nolan et al. | |
| 5,405,367 A | 4/1995 | Schulman et al. | |
| 5,411,031 A | 5/1995 | Yomtov | |
| 5,411,525 A | 5/1995 | Swanson et al. | |
| 5,411,535 A | 5/1995 | Fujii et al. | |
| 5,456,691 A | 10/1995 | Snell | |
| 5,458,622 A | 10/1995 | Alt | |
| 5,466,246 A | 11/1995 | Silvian | |
| 5,468,254 A | 11/1995 | Hahn et al. | |
| 5,472,453 A | 12/1995 | Alt | |
| 5,522,866 A | 6/1996 | Fernald | |
| 5,540,727 A | 7/1996 | Tockman et al. | |
| 5,545,186 A | 8/1996 | Olson et al. | |
| 5,545,202 A | 8/1996 | Dahl et al. | |
| 5,571,146 A | 11/1996 | Jones et al. | |
| 5,591,214 A | 1/1997 | Lu | |
| 5,620,466 A | 4/1997 | Haefner et al. | |
| 5,634,938 A | 6/1997 | Swanson et al. | |
| 5,649,968 A | 7/1997 | Alt et al. | |
| 5,662,688 A | 9/1997 | Haefner et al. | |
| 5,674,259 A | 10/1997 | Gray | |
| 5,683,426 A | 11/1997 | Greenhut et al. | |
| 5,683,432 A | 11/1997 | Goedeke et al. | |
| 5,706,823 A | 1/1998 | Wodlinger | |
| 5,709,215 A | 1/1998 | Perttu et al. | |
| 5,720,770 A | 2/1998 | Nappholz et al. | |
| 5,728,154 A | 3/1998 | Crossett et al. | |
| 5,741,314 A | 4/1998 | Daly et al. | |
| 5,741,315 A | 4/1998 | Lee et al. | |
| 5,752,976 A | 5/1998 | Duffin et al. | |
| 5,752,977 A | 5/1998 | Grevious et al. | |
| 5,755,736 A | 5/1998 | Gillberg et al. | |
| 5,759,199 A | 6/1998 | Snell et al. | |
| 5,774,501 A | 6/1998 | Halpern et al. | |
| 5,792,195 A | 8/1998 | Carlson et al. | |
| 5,792,202 A | 8/1998 | Rueter | |
| 5,792,203 A | 8/1998 | Schroeppel | |
| 5,792,205 A | 8/1998 | Alt et al. | |
| 5,792,208 A | 8/1998 | Gray | |
| 5,814,089 A | 9/1998 | Stokes et al. | |
| 5,827,216 A | 10/1998 | Igo et al. | |
| 5,836,985 A | 11/1998 | Goyal et al. | |
| 5,836,987 A | 11/1998 | Baumann et al. | |
| 5,842,977 A | 12/1998 | Lesho et al. | |
| 5,855,593 A | 1/1999 | Olson et al. | |
| 5,873,894 A | 2/1999 | Vandegriff et al. | |
| 5,891,184 A | 4/1999 | Lee et al. | |
| 5,897,586 A | 4/1999 | Molina | |
| 5,899,876 A | 5/1999 | Flower | |
| 5,899,928 A | 5/1999 | Sholder et al. | |
| 5,919,214 A | 7/1999 | Ciciarelli et al. | |
| 5,935,078 A | 8/1999 | Feierbach | |
| 5,941,906 A | 8/1999 | Barreras et al. | |
| 5,944,744 A | 8/1999 | Paul et al. | |
| 5,954,757 A | 9/1999 | Gray | |
| 5,978,713 A | 11/1999 | Prutchi et al. | |
| 5,991,660 A | 11/1999 | Goyal | |
| 5,991,661 A | 11/1999 | Park et al. | |
| 5,999,848 A | 12/1999 | Gord et al. | |
| 5,999,857 A | 12/1999 | Weijand et al. | |
| 6,016,445 A | 1/2000 | Baura | |
| 6,026,320 A | 2/2000 | Carlson et al. | |
| 6,029,085 A | 2/2000 | Olson et al. | |
| 6,041,250 A | 3/2000 | dePinto | |
| 6,044,298 A | 3/2000 | Salo et al. | |
| 6,044,300 A | 3/2000 | Gray | |
| 6,055,454 A | 4/2000 | Heemels | |
| 6,073,050 A | 6/2000 | Griffith | |
| 6,076,016 A | 6/2000 | Feierbach | |
| 6,077,236 A | 6/2000 | Cunningham | |
| 6,080,187 A | 6/2000 | Alt et al. | |
| 6,083,248 A | 7/2000 | Thompson | |
| 6,106,551 A | 8/2000 | Crossett et al. | |
| 6,115,636 A | 9/2000 | Ryan | |
| 6,128,526 A | 10/2000 | Stadler et al. | |
| 6,141,581 A | 10/2000 | Olson et al. | |
| 6,141,588 A | 10/2000 | Cox et al. | |

(56) References Cited

U.S. PATENT DOCUMENTS

| | | |
|---|---|---|
| 6,141,592 A | 10/2000 | Pauly |
| 6,144,879 A | 11/2000 | Gray |
| 6,162,195 A | 12/2000 | Igo et al. |
| 6,164,284 A | 12/2000 | Schulman et al. |
| 6,167,310 A | 12/2000 | Grevious |
| 6,201,993 B1 | 3/2001 | Kruse et al. |
| 6,208,894 B1 | 3/2001 | Schulman et al. |
| 6,211,799 B1 | 4/2001 | Post et al. |
| 6,221,011 B1 | 4/2001 | Bardy |
| 6,240,316 B1 | 5/2001 | Richmond et al. |
| 6,240,317 B1 | 5/2001 | Villaseca et al. |
| 6,256,534 B1 | 7/2001 | Dahl |
| 6,259,947 B1 | 7/2001 | Olson et al. |
| 6,266,558 B1 | 7/2001 | Gozani et al. |
| 6,266,567 B1 | 7/2001 | Ishikawa et al. |
| 6,270,457 B1 | 8/2001 | Bardy |
| 6,272,377 B1 | 8/2001 | Sweeney et al. |
| 6,273,856 B1 | 8/2001 | Sun et al. |
| 6,277,072 B1 | 8/2001 | Bardy |
| 6,280,380 B1 | 8/2001 | Bardy |
| 6,285,907 B1 | 9/2001 | Kramer et al. |
| 6,292,698 B1 | 9/2001 | Duffin et al. |
| 6,295,473 B1 | 9/2001 | Rosar |
| 6,297,943 B1 | 10/2001 | Carson |
| 6,298,271 B1 | 10/2001 | Weijand |
| 6,307,751 B1 | 10/2001 | Bodony et al. |
| 6,312,378 B1 | 11/2001 | Bardy |
| 6,315,721 B2 | 11/2001 | Schulman et al. |
| 6,336,903 B1 | 1/2002 | Bardy |
| 6,345,202 B2 | 2/2002 | Richmond et al. |
| 6,351,667 B1 | 2/2002 | Godie |
| 6,351,669 B1 | 2/2002 | Hartley et al. |
| 6,353,759 B1 | 3/2002 | Hartley et al. |
| 6,358,203 B2 | 3/2002 | Bardy |
| 6,361,780 B1 | 3/2002 | Ley et al. |
| 6,368,284 B1 | 4/2002 | Bardy |
| 6,371,922 B1 | 4/2002 | Baumann et al. |
| 6,398,728 B1 | 6/2002 | Bardy |
| 6,400,982 B2 | 6/2002 | Sweeney et al. |
| 6,400,990 B1 | 6/2002 | Silvian |
| 6,408,208 B1 | 6/2002 | Sun |
| 6,409,674 B1 | 6/2002 | Brockway et al. |
| 6,411,848 B2 | 6/2002 | Kramer et al. |
| 6,424,865 B1 | 7/2002 | Ding |
| 6,434,429 B1 | 8/2002 | Kraus et al. |
| 6,438,410 B2 | 8/2002 | Hsu et al. |
| 6,438,417 B1 | 8/2002 | Rockwell et al. |
| 6,438,421 B1 | 8/2002 | Stahmann et al. |
| 6,440,066 B1 | 8/2002 | Bardy |
| 6,441,747 B1 | 8/2002 | Khair et al. |
| 6,442,426 B1 | 8/2002 | Kroll |
| 6,442,432 B2 | 8/2002 | Lee |
| 6,443,891 B1 | 9/2002 | Grevious |
| 6,445,953 B1 | 9/2002 | Bulkes et al. |
| 6,453,200 B1 | 9/2002 | Koslar |
| 6,459,929 B1 | 10/2002 | Hopper et al. |
| 6,470,215 B1 | 10/2002 | Kraus et al. |
| 6,471,645 B1 | 10/2002 | Warkentin et al. |
| 6,480,745 B2 | 11/2002 | Nelson et al. |
| 6,487,443 B2 | 11/2002 | Olson et al. |
| 6,490,487 B1 | 12/2002 | Kraus et al. |
| 6,498,951 B1 | 12/2002 | Larson et al. |
| 6,507,755 B1 | 1/2003 | Gozani et al. |
| 6,507,759 B1 | 1/2003 | Prutchi et al. |
| 6,512,940 B1 | 1/2003 | Brabec et al. |
| 6,522,915 B1 | 2/2003 | Ceballos et al. |
| 6,526,311 B2 | 2/2003 | Begemann |
| 6,539,253 B2 | 3/2003 | Thompson et al. |
| 6,542,775 B2 | 4/2003 | Ding et al. |
| 6,553,258 B2 | 4/2003 | Stahmann et al. |
| 6,561,975 B1 | 5/2003 | Pool et al. |
| 6,564,807 B1 | 5/2003 | Schulman et al. |
| 6,574,506 B2 | 6/2003 | Kramer et al. |
| 6,584,351 B1 | 6/2003 | Ekwall |
| 6,584,352 B2 | 6/2003 | Combs et al. |
| 6,597,948 B1 | 7/2003 | Rockwell et al. |
| 6,597,951 B2 | 7/2003 | Kramer et al. |
| 6,622,046 B2 | 9/2003 | Fraley et al. |
| 6,628,985 B2 | 9/2003 | Sweeney et al. |
| 6,647,292 B1 | 11/2003 | Bardy et al. |
| 6,666,844 B1 | 12/2003 | Igo et al. |
| 6,689,117 B2 | 2/2004 | Sweeney et al. |
| 6,690,959 B2 | 2/2004 | Thompson |
| 6,694,189 B2 | 2/2004 | Begemann |
| 6,704,602 B2 | 3/2004 | Berg et al. |
| 6,718,212 B2 | 4/2004 | Parry et al. |
| 6,721,597 B1 | 4/2004 | Bardy et al. |
| 6,738,670 B1 | 5/2004 | Almendinger et al. |
| 6,746,797 B2 | 6/2004 | Benson et al. |
| 6,749,566 B2 | 6/2004 | Russ |
| 6,758,810 B2 | 7/2004 | Lebel et al. |
| 6,763,269 B2 | 7/2004 | Cox |
| 6,778,860 B2 | 8/2004 | Ostroff et al. |
| 6,788,971 B1 | 9/2004 | Sloman et al. |
| 6,788,974 B2 | 9/2004 | Bardy et al. |
| 6,804,558 B2 | 10/2004 | Haller et al. |
| 6,807,442 B1 | 10/2004 | Myklebust et al. |
| 6,847,844 B2 | 1/2005 | Sun et al. |
| 6,871,095 B2 | 3/2005 | Stahmann et al. |
| 6,878,112 B2 | 4/2005 | Linberg et al. |
| 6,885,889 B2 | 4/2005 | Chinchoy |
| 6,892,094 B2 | 5/2005 | Ousdigian et al. |
| 6,897,788 B2 | 5/2005 | Khair et al. |
| 6,904,315 B2 | 6/2005 | Panken et al. |
| 6,922,592 B2 | 7/2005 | Thompson et al. |
| 6,931,282 B2 | 8/2005 | Esler |
| 6,934,585 B1 | 8/2005 | Schloss et al. |
| 6,957,107 B2 | 10/2005 | Rogers et al. |
| 6,978,176 B2 | 12/2005 | Lattouf |
| 6,985,773 B2 | 1/2006 | Von Arx et al. |
| 6,990,375 B2 | 1/2006 | Kloss et al. |
| 7,001,366 B2 | 2/2006 | Ballard |
| 7,003,350 B2 | 2/2006 | Denker et al. |
| 7,006,864 B2 | 2/2006 | Echt et al. |
| 7,013,178 B2 | 3/2006 | Reinke et al. |
| 7,027,871 B2 | 4/2006 | Burnes et al. |
| 7,050,849 B2 | 5/2006 | Echt et al. |
| 7,060,031 B2 | 6/2006 | Webb et al. |
| 7,063,693 B2 | 6/2006 | Guenst |
| 7,082,336 B2 | 7/2006 | Ransbury et al. |
| 7,085,606 B2 | 8/2006 | Flach et al. |
| 7,092,758 B2 | 8/2006 | Sun et al. |
| 7,110,824 B2 | 9/2006 | Amundson et al. |
| 7,120,504 B2 | 10/2006 | Osypka |
| 7,130,681 B2 | 10/2006 | Gebhardt et al. |
| 7,139,613 B2 | 11/2006 | Reinke et al. |
| 7,142,912 B2 | 11/2006 | Wagner et al. |
| 7,146,225 B2 | 12/2006 | Guenst et al. |
| 7,146,226 B2 | 12/2006 | Lau et al. |
| 7,149,581 B2 | 12/2006 | Goedeke |
| 7,149,588 B2 | 12/2006 | Lau et al. |
| 7,158,839 B2 | 1/2007 | Lau |
| 7,162,307 B2 | 1/2007 | Patrias |
| 7,164,952 B2 | 1/2007 | Lau et al. |
| 7,177,700 B1 | 2/2007 | Cox |
| 7,181,505 B2 | 2/2007 | Haller et al. |
| 7,184,830 B2 | 2/2007 | Echt et al. |
| 7,186,214 B2 | 3/2007 | Ness |
| 7,191,015 B2 | 3/2007 | Lamson et al. |
| 7,200,437 B1 | 4/2007 | Nabutovsky et al. |
| 7,200,439 B2 | 4/2007 | Zdeblick et al. |
| 7,206,423 B1 | 4/2007 | Feng et al. |
| 7,209,785 B2 | 4/2007 | Kim et al. |
| 7,209,790 B2 | 4/2007 | Thompson et al. |
| 7,211,884 B1 | 5/2007 | Davis et al. |
| 7,212,871 B1 | 5/2007 | Morgan |
| 7,226,440 B2 | 6/2007 | Gelfand et al. |
| 7,228,183 B2 | 6/2007 | Sun et al. |
| 7,236,821 B2 | 6/2007 | Cates et al. |
| 7,236,829 B1 | 6/2007 | Farazi et al. |
| 7,254,448 B2 | 8/2007 | Almendinger et al. |
| 7,260,436 B2 | 8/2007 | Kilgore et al. |
| 7,270,669 B1 | 9/2007 | Sra |
| 7,272,448 B1 | 9/2007 | Morgan et al. |

(56) References Cited

U.S. PATENT DOCUMENTS

| | | |
|---|---|---|
| 7,277,755 B1 | 10/2007 | Falkenberg et al. |
| 7,280,872 B1 | 10/2007 | Mosesov et al. |
| 7,288,096 B2 | 10/2007 | Chin |
| 7,289,847 B1 | 10/2007 | Gill et al. |
| 7,289,852 B2 | 10/2007 | Helfinstine et al. |
| 7,289,853 B1 | 10/2007 | Campbell et al. |
| 7,289,855 B2 | 10/2007 | Nghiem et al. |
| 7,302,294 B2 | 11/2007 | Kamath et al. |
| 7,305,266 B1 | 12/2007 | Kroll |
| 7,310,556 B2 | 12/2007 | Bulkes |
| 7,319,905 B1 | 1/2008 | Morgan et al. |
| 7,333,853 B2 | 2/2008 | Mazar et al. |
| 7,336,994 B2 | 2/2008 | Hettrick et al. |
| 7,347,819 B2 | 3/2008 | Lebel et al. |
| 7,366,572 B2 | 4/2008 | Heruth et al. |
| 7,373,207 B2 | 5/2008 | Lattouf |
| 7,384,403 B2 | 6/2008 | Sherman |
| 7,386,342 B1 | 6/2008 | Falkenberg et al. |
| 7,392,090 B2 | 6/2008 | Sweeney et al. |
| 7,406,105 B2 | 7/2008 | DelMain et al. |
| 7,406,349 B2 | 7/2008 | Seeberger et al. |
| 7,410,497 B2 | 8/2008 | Hastings et al. |
| 7,425,200 B2 | 9/2008 | Brockway et al. |
| 7,433,739 B1 | 10/2008 | Salys et al. |
| 7,496,409 B2 | 2/2009 | Greenhut et al. |
| 7,496,410 B2 | 2/2009 | Heil |
| 7,502,652 B2 | 3/2009 | Gaunt et al. |
| 7,512,448 B2 | 3/2009 | Malick et al. |
| 7,515,969 B2 | 4/2009 | Tockman et al. |
| 7,526,342 B2 | 4/2009 | Chin et al. |
| 7,529,589 B2 | 5/2009 | Williams et al. |
| 7,532,933 B2 | 5/2009 | Hastings et al. |
| 7,536,222 B2 | 5/2009 | Bardy et al. |
| 7,536,224 B2 | 5/2009 | Ritscher et al. |
| 7,539,541 B2 | 5/2009 | Quiles et al. |
| 7,544,197 B2 | 6/2009 | Kelsch et al. |
| 7,558,631 B2 | 7/2009 | Cowan et al. |
| 7,565,195 B1 | 7/2009 | Kroll et al. |
| 7,584,002 B2 | 9/2009 | Burnes et al. |
| 7,590,455 B2 | 9/2009 | Heruth et al. |
| 7,606,621 B2 | 10/2009 | Brisken et al. |
| 7,610,088 B2 | 10/2009 | Chinchoy |
| 7,610,092 B2 | 10/2009 | Cowan et al. |
| 7,610,099 B2 | 10/2009 | Almendinger et al. |
| 7,610,104 B2 | 10/2009 | Kaplan et al. |
| 7,616,991 B2 | 11/2009 | Mann et al. |
| 7,617,001 B2 | 11/2009 | Penner et al. |
| 7,617,007 B2 | 11/2009 | Williams et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,647,109 B2 | 1/2010 | Hastings et al. |
| 7,650,186 B2 | 1/2010 | Hastings et al. |
| 7,657,311 B2 | 2/2010 | Bardy et al. |
| 7,668,596 B2 | 2/2010 | Von Arx et al. |
| 7,682,316 B2 | 3/2010 | Anderson et al. |
| 7,691,047 B2 | 4/2010 | Ferrari |
| 7,702,392 B2 | 4/2010 | Echt et al. |
| 7,713,194 B2 | 5/2010 | Zdeblick |
| 7,713,195 B2 | 5/2010 | Zdeblick |
| 7,729,783 B2 | 6/2010 | Michels et al. |
| 7,734,333 B2 | 6/2010 | Ghanem et al. |
| 7,734,343 B2 | 6/2010 | Ransbury et al. |
| 7,738,958 B2 | 6/2010 | Zdeblick et al. |
| 7,738,964 B2 | 6/2010 | Von Arx et al. |
| 7,742,812 B2 | 6/2010 | Ghanem et al. |
| 7,742,816 B2 | 6/2010 | Masoud et al. |
| 7,742,822 B2 | 6/2010 | Masoud et al. |
| 7,743,151 B2 | 6/2010 | Vallapureddy et al. |
| 7,747,335 B2 | 6/2010 | Williams |
| 7,751,881 B2 | 7/2010 | Cowan et al. |
| 7,758,521 B2 | 7/2010 | Morris et al. |
| 7,761,150 B2 | 7/2010 | Ghanem et al. |
| 7,761,164 B2 | 7/2010 | Verhoef et al. |
| 7,765,001 B2 | 7/2010 | Echt et al. |
| 7,769,452 B2 | 8/2010 | Ghanem et al. |
| 7,783,362 B2 | 8/2010 | Whitehurst et al. |
| 7,792,588 B2 | 9/2010 | Harding |
| 7,797,059 B1 | 9/2010 | Bornzin et al. |
| 7,801,596 B2 | 9/2010 | Fischell et al. |
| 7,809,438 B2 | 10/2010 | Echt et al. |
| 7,840,281 B2 | 11/2010 | Kveen et al. |
| 7,844,331 B2 | 11/2010 | Li et al. |
| 7,844,348 B2 | 11/2010 | Swoyer et al. |
| 7,846,088 B2 | 12/2010 | Ness |
| 7,848,815 B2 | 12/2010 | Brisken et al. |
| 7,848,823 B2 | 12/2010 | Drasler et al. |
| 7,860,455 B2 | 12/2010 | Fukumoto et al. |
| 7,871,433 B2 | 1/2011 | Lattouf |
| 7,877,136 B1 | 1/2011 | Moffitt et al. |
| 7,877,142 B2 | 1/2011 | Moaddeb et al. |
| 7,881,786 B2 | 2/2011 | Jackson |
| 7,881,798 B2 | 2/2011 | Miesel et al. |
| 7,881,810 B1 | 2/2011 | Chitre et al. |
| 7,890,173 B2 | 2/2011 | Brisken et al. |
| 7,890,181 B2 | 2/2011 | Denzene et al. |
| 7,890,192 B1 | 2/2011 | Kelsch et al. |
| 7,894,885 B2 | 2/2011 | Bartal et al. |
| 7,894,894 B2 | 2/2011 | Stadler et al. |
| 7,894,907 B2 | 2/2011 | Cowan et al. |
| 7,894,910 B2 | 2/2011 | Cowan et al. |
| 7,894,915 B1 | 2/2011 | Chitre et al. |
| 7,899,537 B1 | 3/2011 | Kroll et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,901,360 B1 | 3/2011 | Yang et al. |
| 7,904,170 B2 | 3/2011 | Harding |
| 7,907,993 B2 | 3/2011 | Ghanem et al. |
| 7,920,928 B1 | 4/2011 | Yang et al. |
| 7,925,343 B1 | 4/2011 | Min et al. |
| 7,930,022 B2 | 4/2011 | Zhang et al. |
| 7,930,040 B1 | 4/2011 | Kelsch et al. |
| 7,937,135 B2 | 5/2011 | Ghanem et al. |
| 7,937,148 B2 | 5/2011 | Jacobson |
| 7,937,161 B2 | 5/2011 | Hastings et al. |
| 7,941,214 B2 | 5/2011 | Kleckner et al. |
| 7,945,333 B2 | 5/2011 | Jacobson |
| 7,946,997 B2 | 5/2011 | Hübinette |
| 7,949,404 B2 | 5/2011 | Hill |
| 7,949,405 B2 | 5/2011 | Feher |
| 7,953,486 B2 | 5/2011 | Daum et al. |
| 7,953,493 B2 | 5/2011 | Fowler et al. |
| 7,962,202 B2 | 6/2011 | Bhunia |
| 7,974,702 B1 | 7/2011 | Fain et al. |
| 7,979,136 B2 | 7/2011 | Young et al. |
| 7,983,753 B2 | 7/2011 | Severin |
| 3,010,209 A1 | 8/2011 | Jacobson |
| 7,991,467 B2 | 8/2011 | Markowitz et al. |
| 7,991,471 B2 | 8/2011 | Ghanem et al. |
| 7,996,087 B2 | 8/2011 | Cowan et al. |
| 8,000,791 B2 | 8/2011 | Sunagawa et al. |
| 8,000,807 B2 | 8/2011 | Morris et al. |
| 8,001,975 B2 | 8/2011 | DiSilvestro et al. |
| 8,002,700 B2 | 8/2011 | Ferek-Petric et al. |
| 8,019,419 B1 | 9/2011 | Panescu et al. |
| 8,019,434 B2 | 9/2011 | Quiles et al. |
| 8,027,727 B2 | 9/2011 | Freeberg |
| 8,027,729 B2 | 9/2011 | Sunagawa et al. |
| 8,032,219 B2 | 10/2011 | Neumann et al. |
| 8,036,743 B2 | 10/2011 | Savage et al. |
| 8,046,079 B2 | 10/2011 | Bange et al. |
| 8,046,080 B2 | 10/2011 | Von Arx et al. |
| 8,050,297 B2 | 11/2011 | Delmain et al. |
| 8,050,759 B2 | 11/2011 | Stegemann et al. |
| 8,050,774 B2 | 11/2011 | Kveen et al. |
| 8,055,345 B2 | 11/2011 | Li et al. |
| 8,055,350 B2 | 11/2011 | Roberts |
| 8,060,212 B1 | 11/2011 | Rios et al. |
| 8,065,018 B2 | 11/2011 | Haubrich et al. |
| 8,073,542 B2 | 12/2011 | Doerr |
| 8,078,278 B2 | 12/2011 | Penner |
| 8,078,283 B2 | 12/2011 | Cowan et al. |

(56) References Cited

U.S. PATENT DOCUMENTS

| | | |
|---|---|---|
| 8,095,123 B2 | 1/2012 | Gray |
| 8,102,789 B2 | 1/2012 | Rosar et al. |
| 8,103,359 B2 | 1/2012 | Reddy |
| 8,103,361 B2 | 1/2012 | Moser |
| 8,112,148 B2 | 2/2012 | Giftakis et al. |
| 8,114,021 B2 | 2/2012 | Robertson et al. |
| 8,121,680 B2 | 2/2012 | Falkenberg et al. |
| 8,123,684 B2 | 2/2012 | Zdeblick |
| 8,126,545 B2 | 2/2012 | Flach et al. |
| 8,131,334 B2 | 3/2012 | Lu et al. |
| 8,140,161 B2 | 3/2012 | Willerton et al. |
| 8,150,521 B2 | 4/2012 | Crowley et al. |
| 8,160,672 B2 | 4/2012 | Kim et al. |
| 8,160,702 B2 | 4/2012 | Mann et al. |
| 8,160,704 B2 | 4/2012 | Freeberg |
| 8,165,694 B2 | 4/2012 | Carbanaru et al. |
| 8,175,715 B1 | 5/2012 | Cox |
| 8,180,451 B2 | 5/2012 | Hickman et al. |
| 8,185,213 B2 | 5/2012 | Kveen et al. |
| 8,187,161 B2 | 5/2012 | Li et al. |
| 8,195,293 B2 | 6/2012 | Limousin et al. |
| 8,204,595 B2 | 6/2012 | Pianca et al. |
| 8,204,605 B2 | 6/2012 | Hastings et al. |
| 8,209,014 B2 | 6/2012 | Doerr |
| 8,214,043 B2 | 7/2012 | Matos |
| 8,224,244 B2 | 7/2012 | Kim et al. |
| 8,229,556 B2 | 7/2012 | Li |
| 8,233,985 B2 | 7/2012 | Bulkes et al. |
| 8,265,748 B2 | 9/2012 | Liu et al. |
| 8,265,757 B2 | 9/2012 | Mass et al. |
| 8,262,578 B1 | 10/2012 | Bharmi et al. |
| 8,280,521 B2 | 10/2012 | Haubrich et al. |
| 8,285,387 B2 | 10/2012 | Utsi et al. |
| 8,290,598 B2 | 10/2012 | Boon et al. |
| 8,290,600 B2 | 10/2012 | Hastings et al. |
| 8,295,939 B2 | 10/2012 | Jacobson |
| 8,301,254 B2 | 10/2012 | Mosesov et al. |
| 8,315,701 B2 | 11/2012 | Cowan et al. |
| 8,315,708 B2 | 11/2012 | Berthelsdorf et al. |
| 8,321,021 B2 | 11/2012 | Kisker et al. |
| 8,321,036 B2 | 11/2012 | Brockway et al. |
| 8,332,036 B2 | 12/2012 | Hastings et al. |
| 8,335,563 B2 | 12/2012 | Stessman |
| 8,335,568 B2 | 12/2012 | Heruth et al. |
| 8,340,750 B2 | 12/2012 | Prakash et al. |
| 8,340,780 B2 | 12/2012 | Hastings et al. |
| 8,352,025 B2 | 1/2013 | Jacobson |
| 8,352,028 B2 | 1/2013 | Wenger |
| 8,352,038 B2 | 1/2013 | Mao et al. |
| 8,359,098 B2 | 1/2013 | Lund et al. |
| 8,364,261 B2 | 1/2013 | Stubbs et al. |
| 8,364,276 B2 | 1/2013 | Willis |
| 8,369,959 B2 | 2/2013 | Meskens |
| 8,369,962 B2 | 2/2013 | Abrahamson |
| 8,380,320 B2 | 2/2013 | Spital |
| 8,386,051 B2 | 2/2013 | Rys |
| 8,391,981 B2 | 3/2013 | Mosesov |
| 8,391,990 B2 | 3/2013 | Smith et al. |
| 8,406,874 B2 | 3/2013 | Liu et al. |
| 8,406,879 B2 | 3/2013 | Shuros et al. |
| 8,406,886 B2 | 3/2013 | Gaunt et al. |
| 8,412,352 B2 | 4/2013 | Griswold et al. |
| 8,417,340 B2 | 4/2013 | Goossen |
| 8,417,341 B2 | 4/2013 | Freeberg |
| 8,423,149 B2 | 4/2013 | Hennig |
| 8,428,722 B2 | 4/2013 | Verhoef et al. |
| 8,433,402 B2 | 4/2013 | Ruben et al. |
| 8,433,409 B2 | 4/2013 | Johnson et al. |
| 8,433,420 B2 | 4/2013 | Bange et al. |
| 8,447,412 B2 | 5/2013 | Dal Molin et al. |
| 8,452,413 B2 | 5/2013 | Young et al. |
| 8,457,740 B2 | 6/2013 | Osche |
| 8,457,742 B2 | 6/2013 | Jacobson |
| 8,457,744 B2 | 6/2013 | Janzig et al. |
| 8,457,761 B2 | 6/2013 | Wariar |
| 8,478,407 B2 | 7/2013 | Demmer et al. |
| 8,478,408 B2 | 7/2013 | Hastings et al. |
| 8,478,431 B2 | 7/2013 | Griswold et al. |
| 8,494,632 B2 | 7/2013 | Sun et al. |
| 8,504,156 B2 | 8/2013 | Bonner et al. |
| 8,509,910 B2 | 8/2013 | Sowder et al. |
| 8,515,559 B2 | 8/2013 | Roberts et al. |
| 8,525,340 B2 | 9/2013 | Eckhardt et al. |
| 8,527,068 B2 | 9/2013 | Ostroff |
| 8,532,790 B2 | 9/2013 | Griswold |
| 8,538,526 B2 | 9/2013 | Stahmann et al. |
| 8,541,131 B2 | 9/2013 | Lund et al. |
| 8,543,205 B2 | 9/2013 | Ostroff |
| 8,547,248 B2 | 10/2013 | Zdeblick et al. |
| 8,548,605 B2 | 10/2013 | Ollivier |
| 8,554,333 B2 | 10/2013 | Wu et al. |
| 8,565,882 B2 | 10/2013 | Matos |
| 8,565,897 B2 | 10/2013 | Regnier et al. |
| 8,571,678 B2 | 10/2013 | Wang |
| 8,577,327 B2 | 11/2013 | Makdissi et al. |
| 8,588,926 B2 | 11/2013 | Moore et al. |
| 8,612,002 B2 | 12/2013 | Faltys et al. |
| 8,615,310 B2 | 12/2013 | Khairkhahan et al. |
| 8,626,280 B2 | 1/2014 | Allavatam et al. |
| 8,626,294 B2 | 1/2014 | Sheldon et al. |
| 8,634,908 B2 | 1/2014 | Cowan |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,644,934 B2 | 2/2014 | Hastings et al. |
| 8,649,859 B2 | 2/2014 | Smith et al. |
| 8,670,842 B1 | 3/2014 | Bornzin et al. |
| 8,676,319 B2 | 3/2014 | Knoll |
| 8,676,335 B2 | 3/2014 | Katoozi et al. |
| 8,700,173 B2 | 4/2014 | Edlund |
| 8,700,181 B2 | 4/2014 | Bornzin et al. |
| 8,705,599 B2 | 4/2014 | dal Molin et al. |
| 8,718,766 B2 | 5/2014 | Wahlberg |
| 8,718,773 B2 | 5/2014 | Willis et al. |
| 8,725,260 B2 | 5/2014 | Shuros et al. |
| 8,738,133 B2 | 5/2014 | Shuros et al. |
| 8,738,147 B2 | 5/2014 | Hastings et al. |
| 8,744,555 B2 | 6/2014 | Allavatam et al. |
| 8,744,572 B1 | 6/2014 | Greenhut et al. |
| 8,747,314 B2 | 6/2014 | Stahmann et al. |
| 8,755,884 B2 | 6/2014 | Demmer et al. |
| 8,758,365 B2 | 6/2014 | Bonner et al. |
| 8,768,483 B2 | 7/2014 | Schmitt et al. |
| 8,774,572 B2 | 7/2014 | Hamamoto |
| 8,781,605 B2 | 7/2014 | Bornzin et al. |
| 8,788,035 B2 | 7/2014 | Jacobson |
| 8,788,053 B2 | 7/2014 | Jacobson |
| 8,798,740 B2 | 8/2014 | Samade et al. |
| 8,798,745 B2 | 8/2014 | Jacobson |
| 8,798,762 B2 | 8/2014 | Fain et al. |
| 8,798,770 B2 | 8/2014 | Reddy |
| 8,805,505 B1 | 8/2014 | Roberts |
| 8,805,528 B2 | 8/2014 | Corndorf |
| 8,812,109 B2 | 8/2014 | Blomqvist et al. |
| 8,818,504 B2 | 8/2014 | Bodner et al. |
| 8,827,913 B2 | 9/2014 | Havel et al. |
| 8,831,747 B1 | 9/2014 | Min et al. |
| 8,855,789 B2 | 10/2014 | Jacobson |
| 8,868,186 B2 | 10/2014 | Kroll |
| 8,886,339 B2 | 11/2014 | Faltys et al. |
| 8,903,473 B2 | 12/2014 | Rogers et al. |
| 8,903,500 B2 | 12/2014 | Smith et al. |
| 8,903,513 B2 | 12/2014 | Ollivier |
| 8,909,336 B2 | 12/2014 | Navarro-Paredes et al. |
| 8,914,131 B2 | 12/2014 | Bornzin et al. |
| 8,923,795 B2 | 12/2014 | Makdissi et al. |
| 8,923,963 B2 | 12/2014 | Bonner et al. |
| 8,938,300 B2 | 1/2015 | Rosero |
| 8,942,806 B2 | 1/2015 | Sheldon et al. |
| 8,958,892 B2 | 2/2015 | Khairkhahan et al. |
| 8,977,358 B2 | 3/2015 | Ewert et al. |
| 8,989,873 B2 | 3/2015 | Locsin |
| 8,996,109 B2 | 3/2015 | Karst et al. |
| 9,002,467 B2 | 4/2015 | Smith et al. |

(56) References Cited

U.S. PATENT DOCUMENTS

| | | |
|---|---|---|
| 9,008,776 B2 | 4/2015 | Cowan et al. |
| 9,008,777 B2 | 4/2015 | Dianaty et al. |
| 9,014,818 B2 | 4/2015 | Deterre et al. |
| 9,017,341 B2 | 4/2015 | Bornzin et al. |
| 9,020,611 B2 | 4/2015 | Khairkhahan et al. |
| 9,037,262 B2 | 5/2015 | Regnier et al. |
| 9,042,984 B2 | 5/2015 | Demmer et al. |
| 9,072,911 B2 | 7/2015 | Hastings et al. |
| 9,072,913 B2 | 7/2015 | Jacobson |
| 9,155,882 B2 | 10/2015 | Grubac et al. |
| 9,168,372 B2 | 10/2015 | Fain |
| 9,168,380 B1 | 10/2015 | Greenhut et al. |
| 9,168,383 B2 | 10/2015 | Jacobson et al. |
| 9,180,285 B2 | 11/2015 | Moore et al. |
| 9,192,774 B2 | 11/2015 | Jacobson |
| 9,205,225 B2 | 12/2015 | Khairkhahan et al. |
| 9,216,285 B1 | 12/2015 | Boling et al. |
| 9,216,293 B2 | 12/2015 | Berthiaume et al. |
| 9,216,298 B2 | 12/2015 | Jacobson |
| 9,227,077 B2 | 1/2016 | Jacobson |
| 9,238,145 B2 | 1/2016 | Wenzel et al. |
| 9,242,102 B2 | 1/2016 | Khairkhahan et al. |
| 9,242,113 B2 | 1/2016 | Smith et al. |
| 9,248,300 B2 | 2/2016 | Rys et al. |
| 9,265,436 B2 | 2/2016 | Min et al. |
| 9,265,962 B2 | 2/2016 | Dianaty et al. |
| 9,272,155 B2 | 3/2016 | Ostroff |
| 9,278,218 B2 | 3/2016 | Karst et al. |
| 9,278,229 B1 | 3/2016 | Reinke et al. |
| 9,283,381 B2 | 3/2016 | Grubac et al. |
| 9,283,382 B2 | 3/2016 | Berthiaume et al. |
| 9,289,612 B1 | 3/2016 | Sambelashvili et al. |
| 9,302,115 B2 | 4/2016 | Molin et al. |
| 9,333,364 B2 | 5/2016 | Echt et al. |
| 9,358,387 B2 | 6/2016 | Suwito et al. |
| 9,358,400 B2 | 6/2016 | Jacobson |
| 9,364,675 B2 | 6/2016 | Deterre et al. |
| 9,370,663 B2 | 6/2016 | Moulder |
| 9,375,580 B2 | 6/2016 | Bonner et al. |
| 9,375,581 B2 | 6/2016 | Baru et al. |
| 9,381,365 B2 | 7/2016 | Kibler et al. |
| 9,393,424 B2 | 7/2016 | Demmer et al. |
| 9,393,436 B2 | 7/2016 | Doerr |
| 9,399,139 B2 | 7/2016 | Demmer et al. |
| 9,399,140 B2 | 7/2016 | Cho et al. |
| 9,409,033 B2 | 8/2016 | Jacobson |
| 9,427,594 B1 | 8/2016 | Bornzin et al. |
| 9,433,368 B2 | 9/2016 | Stahmann et al. |
| 9,433,780 B2 | 9/2016 | Régnier et al. |
| 9,492,668 B2 | 11/2016 | Sheldon et al. |
| 9,492,669 B2 | 11/2016 | Demmer et al. |
| 9,492,674 B2 | 11/2016 | Schmidt et al. |
| 9,492,677 B2 | 11/2016 | Greenhut et al. |
| 2002/0032470 A1 | 3/2002 | Linberg |
| 2002/0035376 A1 | 3/2002 | Bardy et al. |
| 2002/0035377 A1 | 3/2002 | Bardy et al. |
| 2002/0035378 A1 | 3/2002 | Bardy et al. |
| 2002/0035380 A1 | 3/2002 | Rissmann et al. |
| 2002/0035381 A1 | 3/2002 | Bardy et al. |
| 2002/0042629 A1 | 4/2002 | Bardy et al. |
| 2002/0042630 A1 | 4/2002 | Bardy et al. |
| 2002/0042634 A1 | 4/2002 | Bardy et al. |
| 2002/0049475 A1 | 4/2002 | Bardy et al. |
| 2002/0052636 A1 | 5/2002 | Bardy et al. |
| 2002/0068958 A1 | 6/2002 | Bardy et al. |
| 2002/0072773 A1 | 6/2002 | Bardy et al. |
| 2002/0082665 A1 | 6/2002 | Haller et al. |
| 2002/0091414 A1 | 7/2002 | Bardy et al. |
| 2002/0095196 A1 | 7/2002 | Linberg |
| 2002/0099423 A1 | 7/2002 | Berg et al. |
| 2002/0103510 A1 | 8/2002 | Bardy et al. |
| 2002/0107545 A1 | 8/2002 | Rissmann et al. |
| 2002/0107546 A1 | 8/2002 | Ostroff et al. |
| 2002/0107547 A1 | 8/2002 | Erlinger et al. |
| 2002/0107548 A1 | 8/2002 | Bardy et al. |
| 2002/0107549 A1 | 8/2002 | Bardy et al. |
| 2002/0107559 A1 | 8/2002 | Sanders et al. |
| 2002/0120299 A1 | 8/2002 | Ostroff et al. |
| 2002/0173830 A1 | 11/2002 | Starkweather et al. |
| 2002/0193846 A1 | 12/2002 | Pool et al. |
| 2003/0009203 A1 | 1/2003 | Lebel et al. |
| 2003/0028082 A1 | 2/2003 | Thompson |
| 2003/0040779 A1 | 2/2003 | Engmark et al. |
| 2003/0041866 A1 | 3/2003 | Linberg et al. |
| 2003/0045805 A1 | 3/2003 | Sheldon et al. |
| 2003/0088278 A1 | 5/2003 | Bardy et al. |
| 2003/0097153 A1 | 5/2003 | Bardy et al. |
| 2003/0105497 A1 | 6/2003 | Zhu et al. |
| 2003/0114908 A1 | 6/2003 | Flach |
| 2003/0144701 A1 | 7/2003 | Mehra et al. |
| 2003/0187460 A1 | 10/2003 | Chin et al. |
| 2003/0187461 A1 | 10/2003 | Chin |
| 2004/0024435 A1 | 2/2004 | Leckrone et al. |
| 2004/0068302 A1 | 4/2004 | Rodgers et al. |
| 2004/0087938 A1 | 5/2004 | Leckrone et al. |
| 2004/0088035 A1 | 5/2004 | Guenst et al. |
| 2004/0102830 A1 | 5/2004 | Williams |
| 2004/0127959 A1 | 7/2004 | Amundson et al. |
| 2004/0133242 A1 | 7/2004 | Chapman et al. |
| 2004/0147969 A1 | 7/2004 | Mann et al. |
| 2004/0147973 A1 | 7/2004 | Hauser |
| 2004/0167558 A1 | 8/2004 | Igo et al. |
| 2004/0167587 A1 | 8/2004 | Thompson |
| 2004/0172071 A1 | 9/2004 | Bardy et al. |
| 2004/0172077 A1 | 9/2004 | Chinchoy |
| 2004/0172104 A1 | 9/2004 | Berg et al. |
| 2004/0176817 A1 | 9/2004 | Wahlstrand et al. |
| 2004/0176818 A1 | 9/2004 | Wahlstrand et al. |
| 2004/0176830 A1 | 9/2004 | Fang |
| 2004/0186529 A1 | 9/2004 | Bardy et al. |
| 2004/0204673 A1 | 10/2004 | Flaherty |
| 2004/0210292 A1 | 10/2004 | Bardy et al. |
| 2004/0210293 A1 | 10/2004 | Bardy et al. |
| 2004/0210294 A1 | 10/2004 | Bardy et al. |
| 2004/0215308 A1 | 10/2004 | Bardy et al. |
| 2004/0220624 A1 | 11/2004 | Ritscher et al. |
| 2004/0220626 A1 | 11/2004 | Wagner |
| 2004/0220639 A1 | 11/2004 | Mulligan et al. |
| 2004/0249431 A1 | 12/2004 | Ransbury et al. |
| 2004/0260348 A1 | 12/2004 | Bakken et al. |
| 2004/0267303 A1 | 12/2004 | Guenst |
| 2005/0061320 A1 | 3/2005 | Lee et al. |
| 2005/0070962 A1 | 3/2005 | Echt et al. |
| 2005/0102003 A1 | 5/2005 | Grabek et al. |
| 2005/0149138 A1 | 7/2005 | Min et al. |
| 2005/0165466 A1 | 7/2005 | Morris et al. |
| 2005/0182465 A1 | 8/2005 | Ness |
| 2005/0203410 A1 | 9/2005 | Jenkins |
| 2005/0283208 A1 | 12/2005 | Von Arx et al. |
| 2005/0288743 A1 | 12/2005 | Ahn et al. |
| 2006/0042830 A1 | 3/2006 | Maghribi et al. |
| 2006/0052829 A1 | 3/2006 | Sun et al. |
| 2006/0052830 A1 | 3/2006 | Spinelli et al. |
| 2006/0064135 A1 | 3/2006 | Brockway |
| 2006/0064149 A1 | 3/2006 | Belacazar et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0095078 A1 | 5/2006 | Tronnes |
| 2006/0106442 A1 | 5/2006 | Richardson et al. |
| 2006/0116746 A1 | 6/2006 | Chin |
| 2006/0135999 A1 | 6/2006 | Bodner et al. |
| 2006/0136004 A1 | 6/2006 | Cowan et al. |
| 2006/0161061 A1 | 7/2006 | Echt et al. |
| 2006/0200002 A1 | 9/2006 | Guenst |
| 2006/0206151 A1 | 9/2006 | Lu |
| 2006/0212079 A1 | 9/2006 | Routh et al. |
| 2006/0241701 A1 | 10/2006 | Markowitz et al. |
| 2006/0241705 A1 | 10/2006 | Neumann et al. |
| 2006/0247672 A1 | 11/2006 | Vidlund et al. |
| 2006/0259088 A1 | 11/2006 | Pastore et al. |
| 2006/0265018 A1 | 11/2006 | Smith et al. |
| 2007/0004979 A1 | 1/2007 | Wojciechowicz et al. |
| 2007/0016098 A1 | 1/2007 | Kim et al. |

(56) References Cited

U.S. PATENT DOCUMENTS

| | | |
|---|---|---|
| 2007/0027508 A1 | 2/2007 | Cowan |
| 2007/0078490 A1 | 4/2007 | Cowan et al. |
| 2007/0088394 A1 | 4/2007 | Jacobson |
| 2007/0088396 A1 | 4/2007 | Jacobson |
| 2007/0088397 A1 | 4/2007 | Jacobson |
| 2007/0088398 A1 | 4/2007 | Jacobson |
| 2007/0088405 A1 | 4/2007 | Jacobson |
| 2007/0135882 A1 | 6/2007 | Drasler et al. |
| 2007/0135883 A1 | 6/2007 | Drasler et al. |
| 2007/0150015 A1* | 6/2007 | Zhang ............... A61N 1/3621 607/17 |
| 2007/0150037 A1 | 6/2007 | Hastings et al. |
| 2007/0150038 A1 | 6/2007 | Hastings et al. |
| 2007/0156190 A1 | 7/2007 | Cinbis |
| 2007/0219525 A1 | 9/2007 | Gelfand et al. |
| 2007/0219590 A1 | 9/2007 | Hastings et al. |
| 2007/0225545 A1 | 9/2007 | Ferrari |
| 2007/0233206 A1 | 10/2007 | Frikart et al. |
| 2007/0239244 A1 | 10/2007 | Morgan et al. |
| 2007/0255376 A1 | 11/2007 | Michels et al. |
| 2007/0276444 A1 | 11/2007 | Gelbart et al. |
| 2007/0293900 A1 | 12/2007 | Sheldon et al. |
| 2007/0293904 A1 | 12/2007 | Gelbart et al. |
| 2008/0004663 A1 | 1/2008 | Jorgenson |
| 2008/0021505 A1 | 1/2008 | Hastings et al. |
| 2008/0021519 A1 | 1/2008 | De Geest et al. |
| 2008/0021532 A1 | 1/2008 | Kveen et al. |
| 2008/0065183 A1 | 3/2008 | Whitehurst et al. |
| 2008/0065185 A1 | 3/2008 | Worley |
| 2008/0071318 A1 | 3/2008 | Brooke et al. |
| 2008/0109054 A1 | 5/2008 | Hastings et al. |
| 2008/0119911 A1 | 5/2008 | Rosero |
| 2008/0130670 A1 | 6/2008 | Kim et al. |
| 2008/0154139 A1 | 6/2008 | Shuros et al. |
| 2008/0154322 A1 | 6/2008 | Jackson et al. |
| 2008/0228234 A1 | 9/2008 | Stancer |
| 2008/0234771 A1 | 9/2008 | Chinchoy et al. |
| 2008/0243217 A1 | 10/2008 | Wildon |
| 2008/0269814 A1 | 10/2008 | Rosero |
| 2008/0269825 A1 | 10/2008 | Chinchoy et al. |
| 2008/0275518 A1 | 11/2008 | Ghanem et al. |
| 2008/0275519 A1 | 11/2008 | Ghanem et al. |
| 2008/0288039 A1 | 11/2008 | Reddy |
| 2008/0294208 A1 | 11/2008 | Willis et al. |
| 2008/0294210 A1 | 11/2008 | Rosero |
| 2008/0306359 A1 | 12/2008 | Zdeblick et al. |
| 2009/0018599 A1 | 1/2009 | Hastings et al. |
| 2009/0024180 A1 | 1/2009 | Kisker et al. |
| 2009/0036941 A1 | 2/2009 | Corbucci |
| 2009/0048646 A1 | 2/2009 | Katoozi et al. |
| 2009/0062895 A1 | 3/2009 | Stahmann et al. |
| 2009/0082827 A1 | 3/2009 | Kveen et al. |
| 2009/0082828 A1 | 3/2009 | Ostroff |
| 2009/0088813 A1 | 4/2009 | Brockway et al. |
| 2009/0131907 A1 | 5/2009 | Chin et al. |
| 2009/0135886 A1 | 5/2009 | Robertson et al. |
| 2009/0143835 A1 | 6/2009 | Pastore et al. |
| 2009/0171408 A1 | 7/2009 | Solem |
| 2009/0171414 A1 | 7/2009 | Kelly et al. |
| 2009/0204163 A1 | 8/2009 | Shuros et al. |
| 2009/0204170 A1 | 8/2009 | Hastings et al. |
| 2009/0210024 A1 | 8/2009 | M |
| 2009/0216292 A1 | 8/2009 | Pless et al. |
| 2009/0234407 A1 | 9/2009 | Hastings et al. |
| 2009/0234411 A1 | 9/2009 | Sambelashvili et al. |
| 2009/0266573 A1 | 10/2009 | Engmark et al. |
| 2009/0275998 A1 | 11/2009 | Burnes et al. |
| 2009/0275999 A1 | 11/2009 | Burnes et al. |
| 2009/0299447 A1 | 12/2009 | Jensen et al. |
| 2010/0013668 A1 | 1/2010 | Kantervik |
| 2010/0016911 A1 | 1/2010 | Willis et al. |
| 2010/0023085 A1 | 1/2010 | Wu et al. |
| 2010/0030061 A1 | 2/2010 | Canfield et al. |
| 2010/0030327 A1 | 2/2010 | Chatel |
| 2010/0042108 A1 | 2/2010 | Hibino |
| 2010/0056871 A1 | 3/2010 | Govari et al. |
| 2010/0063375 A1 | 3/2010 | Kassab et al. |
| 2010/0063562 A1 | 3/2010 | Cowan et al. |
| 2010/0094367 A1 | 4/2010 | Sen |
| 2010/0114209 A1 | 5/2010 | Krause et al. |
| 2010/0114214 A1 | 5/2010 | Morelli et al. |
| 2010/0125281 A1 | 5/2010 | Jacobson et al. |
| 2010/0168761 A1 | 7/2010 | Kassab et al. |
| 2010/0168819 A1 | 7/2010 | Freeberg |
| 2010/0198288 A1 | 8/2010 | Ostroff |
| 2010/0198304 A1 | 8/2010 | Wang |
| 2010/0217367 A1 | 8/2010 | Belson |
| 2010/0228308 A1 | 9/2010 | Cowan et al. |
| 2010/0234906 A1 | 9/2010 | Koh |
| 2010/0234924 A1 | 9/2010 | Willis |
| 2010/0241185 A1 | 9/2010 | Mahapatra et al. |
| 2010/0249729 A1 | 9/2010 | Morris et al. |
| 2010/0286744 A1 | 11/2010 | Echt et al. |
| 2010/0312309 A1 | 12/2010 | Harding |
| 2011/0022113 A1 | 1/2011 | Zdeblick et al. |
| 2011/0071586 A1 | 3/2011 | Jacobson |
| 2011/0077708 A1 | 3/2011 | Ostroff |
| 2011/0112600 A1 | 5/2011 | Cowan et al. |
| 2011/0118588 A1 | 5/2011 | Komblau et al. |
| 2011/0118810 A1 | 5/2011 | Cowan et al. |
| 2011/0137187 A1 | 6/2011 | Yang et al. |
| 2011/0144720 A1 | 6/2011 | Cowan et al. |
| 2011/0152970 A1 | 6/2011 | Jollota et al. |
| 2011/0160558 A1 | 6/2011 | Rassatt et al. |
| 2011/0160565 A1 | 6/2011 | Stubbs et al. |
| 2011/0160801 A1 | 6/2011 | Markowitz et al. |
| 2011/0160806 A1 | 6/2011 | Lyden et al. |
| 2011/0166620 A1 | 7/2011 | Cowan et al. |
| 2011/0166621 A1 | 7/2011 | Cowan et al. |
| 2011/0184491 A1 | 7/2011 | Kivi |
| 2011/0190835 A1 | 8/2011 | Brockway et al. |
| 2011/0208260 A1 | 8/2011 | Jacobson |
| 2011/0218587 A1 | 9/2011 | Jacobson |
| 2011/0230734 A1 | 9/2011 | Fain et al. |
| 2011/0237967 A1 | 9/2011 | Moore et al. |
| 2011/0245890 A1 | 10/2011 | Brisben et al. |
| 2011/0251660 A1 | 10/2011 | Griswold |
| 2011/0251662 A1 | 10/2011 | Griswold et al. |
| 2011/0270099 A1 | 11/2011 | Ruben et al. |
| 2011/0270339 A1 | 11/2011 | Murray, III et al. |
| 2011/0270340 A1 | 11/2011 | Pellegrini et al. |
| 2011/0276102 A1 | 11/2011 | Cohen |
| 2011/0282423 A1 | 11/2011 | Jacobson |
| 2012/0004527 A1 | 1/2012 | Thompson et al. |
| 2012/0029323 A1 | 2/2012 | Zhao |
| 2012/0041508 A1 | 2/2012 | Rousso et al. |
| 2012/0059433 A1 | 3/2012 | Cowan et al. |
| 2012/0059436 A1 | 3/2012 | Fontaine et al. |
| 2012/0065500 A1 | 3/2012 | Rogers et al. |
| 2012/0078322 A1 | 3/2012 | Dal Molin et al. |
| 2012/0089198 A1 | 4/2012 | Ostroff |
| 2012/0093245 A1 | 4/2012 | Makdissi et al. |
| 2012/0095521 A1 | 4/2012 | Hintz |
| 2012/0095539 A1 | 4/2012 | Khairkhahan et al. |
| 2012/0101540 A1 | 4/2012 | O'Brien et al. |
| 2012/0101553 A1 | 4/2012 | Reddy |
| 2012/0109148 A1 | 5/2012 | Bonner et al. |
| 2012/0109149 A1 | 5/2012 | Bonner et al. |
| 2012/0109236 A1 | 5/2012 | Jacobson et al. |
| 2012/0109259 A1 | 5/2012 | Bond et al. |
| 2012/0116489 A1 | 5/2012 | Khairkhahan et al. |
| 2012/0150251 A1 | 6/2012 | Giftakis et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0172942 A1 | 7/2012 | Berg |
| 2012/0197350 A1 | 8/2012 | Roberts et al. |
| 2012/0197373 A1 | 8/2012 | Khairkhahan et al. |
| 2012/0215285 A1 | 8/2012 | Tahmasian et al. |
| 2012/0232565 A1 | 9/2012 | Kveen et al. |
| 2012/0277600 A1 | 11/2012 | Greenhut |
| 2012/0277606 A1 | 11/2012 | Ellingson et al. |

(56) References Cited

U.S. PATENT DOCUMENTS

| | | |
|---|---|---|
| 2012/0283795 A1 | 11/2012 | Stancer et al. |
| 2012/0283807 A1 | 11/2012 | Deterre et al. |
| 2012/0290025 A1 | 11/2012 | Keimel |
| 2012/0296381 A1 | 11/2012 | Matos |
| 2012/0303082 A1 | 11/2012 | Dong et al. |
| 2012/0316613 A1 | 12/2012 | Keefe et al. |
| 2013/0012151 A1 | 1/2013 | Hankins |
| 2013/0023975 A1 | 1/2013 | Locsin |
| 2013/0035748 A1 | 2/2013 | Bonner et al. |
| 2013/0041422 A1 | 2/2013 | Jacobson |
| 2013/0053908 A1 | 2/2013 | Smith et al. |
| 2013/0053915 A1 | 2/2013 | Holmstrom et al. |
| 2013/0053921 A1 | 2/2013 | Bonner et al. |
| 2013/0060298 A1 | 3/2013 | Splett et al. |
| 2013/0066169 A1 | 3/2013 | Rys et al. |
| 2013/0072770 A1 | 3/2013 | Rao et al. |
| 2013/0079798 A1 | 3/2013 | Tran et al. |
| 2013/0079861 A1 | 3/2013 | Reinert et al. |
| 2013/0085350 A1 | 4/2013 | Schugt et al. |
| 2013/0085403 A1 | 4/2013 | Gunderson et al. |
| 2013/0085550 A1 | 4/2013 | Polefko et al. |
| 2013/0096649 A1 | 4/2013 | Martin et al. |
| 2013/0103047 A1 | 4/2013 | Steingisser et al. |
| 2013/0103109 A1 | 4/2013 | Jacobson |
| 2013/0110008 A1 | 5/2013 | Bourget et al. |
| 2013/0110127 A1 | 5/2013 | Bornzin et al. |
| 2013/0110192 A1 | 5/2013 | Tran et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0116741 A1 | 5/2013 | Bornzin et al. |
| 2013/0123872 A1 | 5/2013 | Bornzin et al. |
| 2013/0123875 A1 | 5/2013 | Varady et al. |
| 2013/0131591 A1 | 5/2013 | Berthiaume et al. |
| 2013/0131693 A1 | 5/2013 | Berthiaume et al. |
| 2013/0138006 A1 | 5/2013 | Bornzin et al. |
| 2013/0150695 A1 | 6/2013 | Biela et al. |
| 2013/0150911 A1 | 6/2013 | Perschbacher et al. |
| 2013/0150912 A1 | 6/2013 | Perschbacher et al. |
| 2013/0184776 A1 | 7/2013 | Shuros et al. |
| 2013/0196703 A1 | 8/2013 | Masoud et al. |
| 2013/0197609 A1 | 8/2013 | Moore et al. |
| 2013/0231710 A1 | 9/2013 | Jacobson |
| 2013/0238072 A1 | 9/2013 | Deterre et al. |
| 2013/0238073 A1 | 9/2013 | Makdissi et al. |
| 2013/0253342 A1 | 9/2013 | Griswold et al. |
| 2013/0253343 A1 | 9/2013 | Waldhauser et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0265144 A1 | 10/2013 | Banna et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0296727 A1 | 11/2013 | Sullivan et al. |
| 2013/0303872 A1 | 11/2013 | Taff et al. |
| 2013/0324825 A1 | 12/2013 | Ostroff et al. |
| 2013/0325081 A1* | 12/2013 | Karst .......... A61N 1/36592 607/25 |
| 2013/0345770 A1 | 12/2013 | Dianaty et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0031836 A1 | 1/2014 | Ollivier |
| 2014/0039570 A1 | 2/2014 | Carroll et al. |
| 2014/0039591 A1 | 2/2014 | Drasler et al. |
| 2014/0043146 A1 | 2/2014 | Makdissi et al. |
| 2014/0046395 A1 | 2/2014 | Regnier et al. |
| 2014/0046420 A1 | 2/2014 | Moore et al. |
| 2014/0058240 A1 | 2/2014 | Mothilal et al. |
| 2014/0058494 A1 | 2/2014 | Ostroff et al. |
| 2014/0074114 A1 | 3/2014 | Khairkhahan et al. |
| 2014/0074186 A1 | 3/2014 | Faltys et al. |
| 2014/0094891 A1 | 4/2014 | Pare et al. |
| 2014/0100627 A1 | 4/2014 | Min |
| 2014/0107723 A1 | 4/2014 | Hou et al. |
| 2014/0121719 A1 | 5/2014 | Bonner et al. |
| 2014/0121720 A1 | 5/2014 | Bonner et al. |
| 2014/0121722 A1 | 5/2014 | Sheldon et al. |
| 2014/0128935 A1 | 5/2014 | Kumar et al. |
| 2014/0135865 A1 | 5/2014 | Hastings et al. |
| 2014/0142648 A1 | 5/2014 | Smith et al. |
| 2014/0148675 A1 | 5/2014 | Nordstrom et al. |
| 2014/0148815 A1 | 5/2014 | Wenzel et al. |
| 2014/0155950 A1 | 6/2014 | Hastings et al. |
| 2014/0169162 A1 | 6/2014 | Romano et al. |
| 2014/0172034 A1 | 6/2014 | Bornzin et al. |
| 2014/0172060 A1 | 6/2014 | Bornzin et al. |
| 2014/0180306 A1 | 6/2014 | Grubac et al. |
| 2014/0180366 A1 | 6/2014 | Edlund |
| 2014/0207149 A1 | 7/2014 | Hastings et al. |
| 2014/0207210 A1 | 7/2014 | Willis et al. |
| 2014/0214104 A1 | 7/2014 | Greenhut et al. |
| 2014/0222098 A1 | 8/2014 | Baru et al. |
| 2014/0222109 A1 | 8/2014 | Moulder |
| 2014/0228913 A1 | 8/2014 | Molin et al. |
| 2014/0236172 A1 | 8/2014 | Hastings et al. |
| 2014/0243848 A1 | 8/2014 | Auricchio et al. |
| 2014/0255298 A1 | 9/2014 | Cole et al. |
| 2014/0257324 A1 | 9/2014 | Fain |
| 2014/0257422 A1 | 9/2014 | Herken |
| 2014/0257444 A1 | 9/2014 | Cole et al. |
| 2014/0276929 A1 | 9/2014 | Foster et al. |
| 2014/0303704 A1 | 10/2014 | Suwito et al. |
| 2014/0309706 A1 | 10/2014 | Jacobson |
| 2014/0379041 A1 | 12/2014 | Foster |
| 2015/0025612 A1 | 1/2015 | Haasl et al. |
| 2015/0039041 A1 | 2/2015 | Smith et al. |
| 2015/0051609 A1 | 2/2015 | Schmidt et al. |
| 2015/0051610 A1 | 2/2015 | Schmidt et al. |
| 2015/0051611 A1 | 2/2015 | Schmidt et al. |
| 2015/0051612 A1 | 2/2015 | Schmidt et al. |
| 2015/0051613 A1 | 2/2015 | Schmidt et al. |
| 2015/0051614 A1 | 2/2015 | Schmidt et al. |
| 2015/0051615 A1 | 2/2015 | Schmidt et al. |
| 2015/0051616 A1 | 2/2015 | Haasl et al. |
| 2015/0051682 A1 | 2/2015 | Schmidt et al. |
| 2015/0057520 A1 | 2/2015 | Foster et al. |
| 2015/0057558 A1 | 2/2015 | Stahmann et al. |
| 2015/0057721 A1 | 2/2015 | Stahmann et al. |
| 2015/0088155 A1 | 3/2015 | Stahmann et al. |
| 2015/0105836 A1 | 4/2015 | Bonner et al. |
| 2015/0157861 A1 | 6/2015 | Aghassian |
| 2015/0173655 A1 | 6/2015 | Demmer et al. |
| 2015/0190638 A1 | 7/2015 | Smith et al. |
| 2015/0196756 A1 | 7/2015 | Stahmann et al. |
| 2015/0196757 A1 | 7/2015 | Stahmann et al. |
| 2015/0196758 A1 | 7/2015 | Stahmann et al. |
| 2015/0196769 A1 | 7/2015 | Stahmann et al. |
| 2015/0217119 A1 | 8/2015 | Nikolski et al. |
| 2015/0221898 A1 | 8/2015 | Chi et al. |
| 2015/0224315 A1 | 8/2015 | Stahmann |
| 2015/0224320 A1 | 8/2015 | Stahmann |
| 2015/0258345 A1 | 9/2015 | Smith et al. |
| 2015/0290468 A1 | 10/2015 | Zhang |
| 2015/0297905 A1 | 10/2015 | Greenhut et al. |
| 2015/0297907 A1 | 10/2015 | Zhang |
| 2015/0305637 A1 | 10/2015 | Greenhut et al. |
| 2015/0305638 A1 | 10/2015 | Zhang |
| 2015/0305639 A1 | 10/2015 | Greenhut et al. |
| 2015/0305640 A1 | 10/2015 | Reinke et al. |
| 2015/0305641 A1 | 10/2015 | Stadler et al. |
| 2015/0305642 A1 | 10/2015 | Reinke et al. |
| 2015/0306374 A1 | 10/2015 | Seifert et al. |
| 2015/0306375 A1 | 10/2015 | Marshall et al. |
| 2015/0306406 A1 | 10/2015 | Crutchfield et al. |
| 2015/0306407 A1 | 10/2015 | Crutchfield et al. |
| 2015/0306408 A1 | 10/2015 | Greenhut et al. |
| 2015/0321016 A1 | 11/2015 | O'Brien et al. |

(56) References Cited

U.S. PATENT DOCUMENTS

| | | | |
|---|---|---|---|
| 2015/0328459 A1 | 11/2015 | Chin et al. | |
| 2016/0015322 A1 | 1/2016 | Anderson et al. | |
| 2016/0023000 A1 | 1/2016 | Cho et al. | |
| 2016/0030757 A1 | 2/2016 | Jacobson | |
| 2016/0033177 A1 | 2/2016 | Barot et al. | |
| 2016/0114169 A1* | 4/2016 | Sheldon | A61N 1/3704 607/17 |
| 2016/0121127 A1 | 5/2016 | Klimovitch et al. | |
| 2016/0121128 A1 | 5/2016 | Fishler et al. | |
| 2016/0121129 A1 | 5/2016 | Persson et al. | |
| 2016/0213919 A1 | 7/2016 | Suwito et al. | |
| 2016/0213937 A1 | 7/2016 | Reinke et al. | |
| 2016/0213939 A1 | 7/2016 | Carney et al. | |
| 2016/0228026 A1 | 8/2016 | Jackson | |
| 2016/0317825 A1 | 11/2016 | Jacobson | |

FOREIGN PATENT DOCUMENTS

| | | |
|---|---|---|
| AU | 2014203793 A1 | 7/2014 |
| CA | 1003904 A1 | 1/1977 |
| CN | 202933393 U | 5/2013 |
| EP | 0362611 A1 | 4/1990 |
| EP | 503823 A2 | 9/1992 |
| EP | 1702648 A2 | 9/2006 |
| EP | 1904166 B1 | 6/2011 |
| EP | 2433675 B1 | 1/2013 |
| EP | 2441491 B1 | 1/2013 |
| EP | 2452721 B1 | 11/2013 |
| EP | 1948296 B1 | 1/2014 |
| EP | 2662113 A3 | 1/2014 |
| EP | 2471452 B1 | 12/2014 |
| EP | 2760541 B1 | 5/2016 |
| EP | 2833966 B1 | 5/2016 |
| JP | 2000051373 A | 2/2000 |
| JP | 2002502640 A | 1/2002 |
| JP | 2004512105 A | 4/2004 |
| JP | 2005508208 A | 3/2005 |
| JP | 2005245215 A | 9/2005 |
| JP | 2008540040 A | 11/2008 |
| JP | 5199867 B2 | 2/2013 |
| WO | 9500202 A1 | 1/1995 |
| WO | 9636134 A1 | 11/1996 |
| WO | 9724981 A2 | 7/1997 |
| WO | 9826840 A1 | 6/1998 |
| WO | 9939767 A1 | 8/1999 |
| WO | 0234330 A2 | 1/2003 |
| WO | 02098282 A2 | 5/2003 |
| WO | 2005000206 A3 | 4/2005 |
| WO | 2005042089 A1 | 5/2005 |
| WO | 2006065394 A1 | 6/2006 |
| WO | 2006086435 A3 | 8/2006 |
| WO | 2006113659 A1 | 10/2006 |
| WO | 2006124833 A2 | 11/2006 |
| WO | 2006124833 A3 | 5/2007 |
| WO | 2007075974 A2 | 7/2007 |
| WO | 2009006531 A1 | 1/2009 |
| WO | 2012054102 A1 | 4/2012 |
| WO | 2013080038 A2 | 6/2013 |
| WO | 2013098644 A3 | 8/2013 |
| WO | 2013184787 A1 | 12/2013 |
| WO | 2014120769 A1 | 8/2014 |

OTHER PUBLICATIONS

International Search Report and Written Opinion for Application No. PCT/US2016/056055, 13 pages, dated Jan. 24, 2017.
Hachisuka et al., "Development and Performance Analysis of an Intra-Body Communication Device," The 12th International Conference on Solid State Sensors, Actuators and Microsystems, vol. 4A1.3, pp. 1722-1725, 2003.
Seyedi et al., "A Survey on Intrabody Communications for Body Area Network Application," IEEE Transactions on Biomedical Engineering,vol. 60(8): 2067-2079, 2013.
Wegmüller, "Intra-Body Communication for Biomedical Sensor Networks," Diss. ETH, No. 17323, 1-173, 2007.
Notification of Transmittal of the International Search Report and the Written Opinion of the International Searching Authority, or the Declaration, dated Jan. 29, 2016, 15 pages.
Spickler et al., "Totally Self-Contained Intracardiac Pacemaker," Journal of Electrocardiology, vol. 3(3&4): 324-331, 1970.
"Instructions for Use System 1, Leadless Cardiac Pacemaker (LCP) and Delivery Catheter," Nanostim Leadless Pacemakers, pp. 1-28, 2013.

* cited by examiner

DEVICES AND METHODS FOR ADJUSTING PACING RATES IN AN IMPLANTABLE MEDICAL DEVICE

CROSS REFERENCE TO RELATED APPLICATIONS

This application claims the benefit of U.S. Provisional Patent Application Ser. No. 62/239,025 filed on Oct. 8, 2015, the disclosure of which is incorporated herein by reference.

TECHNICAL FIELD

The present disclosure generally relates to systems, devices, and methods for adjusting a pacing rate of an implantable medical device such as in a rate responsive manner, and more particularly to systems, devices, and methods for limiting the duration of elevated pacing rates in an implantable medical device.

BACKGROUND

Pacing instruments can be used to treat patients suffering from various heart conditions that result in a reduced ability of the heart to deliver sufficient amounts of blood to a patient's body. These heart conditions may lead to rapid, irregular, and/or inefficient heart contractions. To help alleviate some of these conditions, various devices (e.g., pacemakers, defibrillators, etc.) can be implanted in a patient's body. Such devices may monitor and provide electrical stimulation to the heart to help the heart operate in a more normal, efficient and/or safe manner. In some cases, such devices may have a rate response capability that changes the pacing rate based on the current metabolic demand of the patient. In some cases, the devices may be part of an implantable medical device system.

SUMMARY

The present disclosure generally relates to systems, devices, and methods for adjusting a pacing rate of an implantable medical device such as in a rate responsive manner, and more particularly to systems, devices, and methods for limiting the duration of elevated pacing rates in an implantable medical device.

In a first illustrative embodiment, a Leadless Cardiac Pacemaker (LCP) may comprise an outer housing, a plurality of exposed electrodes connected relative to the outer housing, and a controller disposed within the outer housing and operatively connected to the plurality of exposed electrodes. The controller may be configured to: deliver pacing pulses via the plurality of exposed electrodes at a base pacing rate; detect a measure of metabolic demand, wherein the measure of metabolic demand varies over time; deliver pacing pulses at an elevated pacing rate relative to the base pacing rate after determining an elevated metabolic demand with respect to a base measure of metabolic demand, wherein the elevated pacing rate varies with time and is dependent on the detected measure of metabolic demand; change a heart stress tracking value during times when pacing pulses are delivered at the elevated pacing rate, wherein the heart stress tracking value is changed faster during times when higher elevated pacing rates are delivered relative to times when lower elevated pacing rates are delivered; and determine if the heart stress tracking value crosses a predetermined heart stress threshold, and if so, reduce the elevated pacing rate back toward the base pacing rate.

Additionally, or alternatively, in any of the above embodiments with respect to the first illustrative embodiment, the controller may be configured to increase the heart stress tracking value monotonically over time.

Additionally, or alternatively, in any of the above embodiments with respect to the first illustrative embodiment, the controller may be configured to decrease the heart stress tracking value monotonically over time.

Additionally, or alternatively, in any of the above embodiments with respect to the first illustrative embodiment, if the measure of metabolic demand is no longer elevated with respect to the base measure of metabolic demand, the controller may be configured to deliver pacing pulses at the base pacing rate.

Additionally, or alternatively, in any of the above embodiments with respect to the first illustrative embodiment, the controller may be configured to reset the heart stress tracking value if the pacing pulses are no longer being delivered at the elevated pacing rate for at least a predetermined length of time.

Additionally, or alternatively, in any of the above embodiments with respect to the first illustrative embodiment, the controller may be further configured to pause changing the heart stress tracking value if the elevated pacing rate falls below a threshold pacing rate that is higher than the base pacing rate.

Additionally, or alternatively, in any of the above embodiments with respect to the first illustrative embodiment, the LCP may further comprise an accelerometer disposed within the outer housing, and wherein the controller may be configured to detect the measure of metabolic demand by monitoring an output of the accelerometer.

Additionally, or alternatively, in any of the above embodiments with respect to the first illustrative embodiment, the controller may be configured to detect the measure of metabolic demand by monitoring an impedance signal via the plurality of exposed electrodes.

Additionally, or alternatively, in any of the above embodiments with respect to the first illustrative embodiment, the impedance signal provides a measure of respiration rate.

Additionally, or alternatively, in any of the above embodiments with respect to the first illustrative embodiment, the controller may be configured to determine if the heart stress tracking value crosses the predetermined heart stress threshold, and if so, reduce the elevated pacing rate to the base pacing rate.

Additionally, or alternatively, in any of the above embodiments with respect to the first illustrative embodiment, the base pacing rate may be a lower rate limit.

Additionally, or alternatively, in any of the above embodiments with respect to the first illustrative embodiment, a counter may be used to change the heart stress tracking value during times when pacing pulses are delivered at the elevated pacing rate.

Additionally, or alternatively, in any of the above embodiments with respect to the first illustrative embodiment, a counter may be incremented at a faster rate during times when higher elevated pacing rates are delivered relative to times when lower elevated pacing rates are delivered.

In a second illustrative embodiment, a method for adjusting a pacing rate of a medical device may comprise: generating, by the medical device, pacing pulses at a pacing rate that varies over time based on a determined metabolic demand; adjusting, by the medical device, a heart stress tracking value while generating pacing pulses at or above a first pacing rate, wherein a rate of adjustment of the heart stress tracking value is dependent on a current pacing rate; determining, by the medical device, when the heart stress tracking value crosses a predetermined heart stress threshold; and after determining that the heart stress tracking value crossed the predetermined heart stress threshold, generating, by the medical device, pacing pulses at a second pacing rate, wherein the second pacing rate is lower than the first pacing rate.

Additionally, or alternatively, in any of the above embodiments with respect to the second illustrative embodiment, the method may further comprise resetting the heart stress tracking value, by the medical device, after generating pacing pulses at pacing rates below a pacing rate threshold that is below the first pacing rate for a predetermined amount of time.

In a third illustrative embodiment, an implantable medical device for generating pacing pulses to a heart of a patient may comprise a plurality of electrodes for delivering pacing pulses to the heart of the patient, a pulse generator operatively coupled to the plurality of electrodes, and a controller operatively coupled to the pulse generator. The pulse generator may be configured to generate pacing pulses at a current pacing rate and deliver the pacing pulses to the plurality of electrodes. The controller may comprise a pacing rate circuit configured to determine the current pacing rate for the pulse generator and a watchdog circuit. The watchdog circuit may be configured to: monitor the current pacing rate over time, and if the current pacing rate rises above a predetermined pacing rate threshold at a start time and remains above the predetermined pacing rate threshold for a predetermined threshold amount of time, force the current pacing rate of the pulse generator to be at a base pacing rate, and if the current pacing rate falls below the predetermined pacing rate threshold before the predetermined threshold amount of time expires, and remains below the predetermined pacing rate threshold for at least a threshold amount of time, reset the start time to a next time the current pacing rate rises above the predetermined pacing rate threshold.

Additionally, or alternatively, in any of the above embodiments with respect to the third illustrative embodiment, after forcing the current pacing rate of the pulse generator to be at the base pacing rate, the watchdog circuit may be configured to maintain the current pacing rate at the base pacing rate for at least a predetermined rest period of time.

Additionally, or alternatively, in any of the above embodiments with respect to the second illustrative embodiment, the predetermined threshold amount of time may be dependent on the current pacing rate while the current pacing rate remains above the predetermined pacing rate threshold.

Additionally, or alternatively, in any of the above embodiments with respect to the second illustrative embodiment, the pacing rate circuit may determine the current pacing rate in a rate responsive manner.

Additionally, or alternatively, in any of the above embodiments with respect to the second illustrative embodiment, the implantable medical device may be a leadless cardiac pacemaker configured to be implanted on or within a heart.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The disclosure may be more completely understood in consideration of the following description of various illustrative embodiments in connection with the accompanying drawings, in which.

Figure 1:
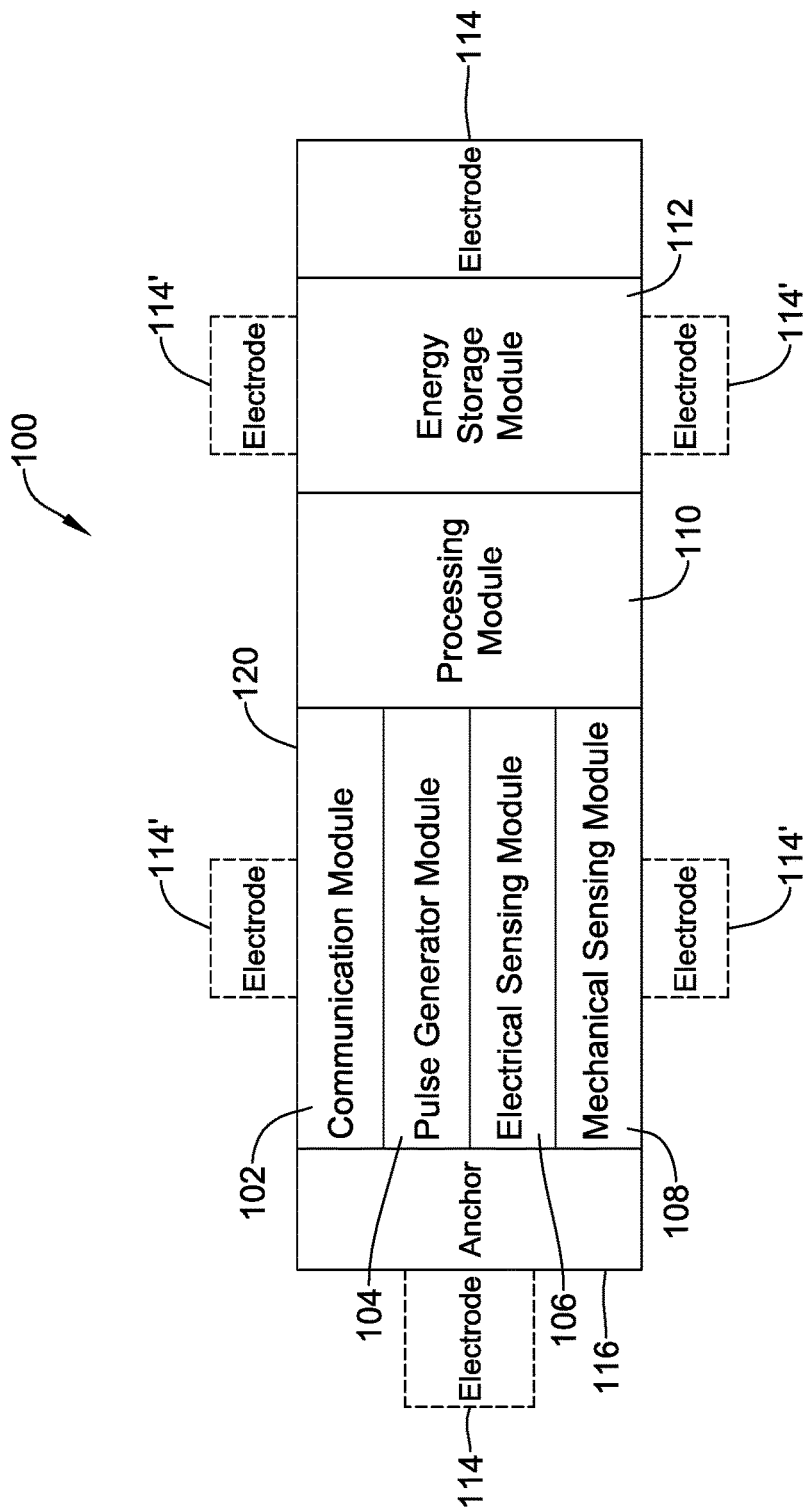
FIG. 1 is a schematic block diagram of an illustrative leadless cardiac pacemaker (LCP) according to one example embodiment of the present disclosure.

While the disclosure is amenable to various modifications and alternative forms, specifics thereof have been shown by way of embodiment in the drawings and will be described in detail. It should be understood, however, that the intention is not to limit aspects of the disclosure to the particular illustrative embodiments described. On the contrary, the intention is to cover all modifications, equivalents, and alternatives falling within the spirit and scope of the disclosure.

DESCRIPTION

The following description should be read with reference to the drawings in which similar elements in different drawings are numbered the same. The description and the drawings, which are not necessarily to scale, depict illustrative embodiments and are not intended to limit the scope of the disclosure.

FIG. 1 is a conceptual schematic block diagram of an exemplary leadless cardiac pacemaker (LCP) that may be implanted on the heart or within a chamber of the heart and may operate to sense physiological signals and parameters and deliver one or more types of electrical stimulation therapy to the heart of the patient. Example electrical stimulation therapy may include bradycardia pacing, rate responsive pacing therapy, cardiac resynchronization therapy (CRT), anti-tachycardia pacing (ATP) therapy and/or the like. As can be seen in FIG. 1, LCP 100 may be a compact device with all components housed within LCP 100 or directly on housing 120. In some instances, LCP 100 may include communication module 102, pulse generator module 104, electrical sensing module 106, mechanical sensing module 108, processing module 110, energy storage module 112, and electrodes 114.

As depicted in FIG. 1, LCP 100 may include electrodes 114, which can be secured relative to housing 120 and electrically exposed to tissue and/or blood surrounding LCP 100. Electrodes 114 may generally conduct electrical signals to and from LCP 100 and the surrounding tissue and/or blood. Such electrical signals can include communication signals, electrical stimulation pulses, and intrinsic cardiac electrical signals, to name a few. Intrinsic cardiac electrical signals may include electrical signals generated by the heart and may be represented by an electrocardiogram (ECG).

Electrodes 114 may include one or more biocompatible conductive materials such as various metals or alloys that are known to be safe for implantation within a human body. In some instances, electrodes 114 may be generally disposed on either end of LCP 100 and may be in electrical communication with one or more of modules 102, 104, 106, 108, and 110. In embodiments where electrodes 114 are secured directly to housing 120, an insulative material may electrically isolate the electrodes 114 from adjacent electrodes, housing 120, and/or other parts of LCP 100. In some instances, some or all of electrodes 114 may be spaced from housing 120 and connected to housing 120 and/or other components of LCP 100 through connecting wires. In such instances, the electrodes 114 may be placed on a tail (not shown) that extends out away from the housing 120. As shown in FIG. 1, in some embodiments, LCP 100 may include electrodes 114'. Electrodes 114' may be in addition to electrodes 114, or may replace one or more of electrodes 114. Electrodes 114' may be similar to electrodes 114 except that electrodes 114' are disposed on the sides of LCP 100. In some cases, electrodes 114' may increase the number of electrodes by which LCP 100 may deliver communication signals and/or electrical stimulation pulses, and/or may sense intrinsic cardiac electrical signals, communication signals, and/or electrical stimulation pulses.

Electrodes 114 and/or 114' may assume any of a variety of sizes and/or shapes, and may be spaced at any of a variety of spacings. For example, electrodes 114 may have an outer diameter of two to twenty millimeters (mm). In other embodiments, electrodes 114 and/or 114' may have a diameter of two, three, five, seven millimeters (mm), or any other suitable diameter, dimension and/or shape. Example lengths for electrodes 114 and/or 114' may include, for example, one, three, five, ten millimeters (mm), or any other suitable length. As used herein, the length is a dimension of electrodes 114 and/or 114' that extends away from the outer surface of the housing 120. In some instances, at least some of electrodes 114 and/or 114' may be spaced from one another by a distance of twenty, thirty, forty, fifty millimeters (mm), or any other suitable spacing. The electrodes 114 and/or 114' of a single device may have different sizes with respect to each other, and the spacing and/or lengths of the electrodes on the device may or may not be uniform.

In the embodiment shown, communication module 102 may be electrically coupled to electrodes 114 and/or 114' and may be configured to deliver communication pulses to tissues of the patient for communicating with other devices such as sensors, programmers, other medical devices, and/or the like. Communication signals, as used herein, may be any modulated signal that conveys information to another device, either by itself or in conjunction with one or more other modulated signals. In some embodiments, communication signals may be limited to sub-threshold signals that do not result in capture of the heart yet still convey information. The communication signals may be delivered to another device that is located either external or internal to the patient's body. In some instances, the communication may take the form of distinct communication pulses separated by various amounts of time. In some of these cases, the timing between successive pulses may convey information. Communication module 102 may additionally be configured to sense for communication signals delivered by other devices, which may be located external or internal to the patient's body.

Communication module 102 may communicate to help accomplish one or more desired functions. Some example functions include delivering sensed data, using communicated data for determining occurrences of events such as arrhythmias, coordinating delivery of electrical stimulation therapy, and/or other functions. In some cases, LCP 100 may use communication signals to communicate raw information, processed information, messages and/or commands, and/or other data. Raw information may include information such as sensed electrical signals (e.g. a sensed ECG), signals gathered from coupled sensors, and the like. In some embodiments, the processed information may include signals that have been filtered using one or more signal processing techniques. Processed information may also include parameters and/or events that are determined by the LCP 100 and/or another device, such as a determined heart rate, timing of determined heartbeats, timing of other determined events, determinations of threshold crossings, expirations of monitored time periods, accelerometer signals, activity level parameters, blood-oxygen parameters, blood pressure parameters, heart sound parameters, and the like. Messages and/or commands may include instructions or the like directing another device to take action, notifications of imminent actions of the sending device, requests for reading from the receiving device, requests for writing data to the receiving device, information messages, and/or other messages commands.

In at least some embodiments, communication module 102 (or LCP 100) may further include switching circuitry to selectively connect one or more of electrodes 114 and/or 114' to communication module 102 in order to select which electrodes 114 and/or 114' that communication module 102 delivers communication pulses. It is contemplated that communication module 102 may be communicating with other devices via conducted signals, radio frequency (RF) signals, optical signals, acoustic signals, inductive coupling, and/or any other suitable communication methodology. Where communication module 102 generates electrical communication signals, communication module 102 may include one or more capacitor elements and/or other charge storage devices to aid in generating and delivering communication signals. In the embodiment shown, communication module 102 may use energy stored in energy storage module 112 to generate the communication signals. In at least some examples, communication module 102 may include a switching circuit that is connected to energy storage module 112 and, with the switching circuitry, may connect energy storage module 112 to one or more of electrodes 114/114' to generate the communication signals.

As shown in FIG. 1, a pulse generator module 104 may be electrically connected to one or more of electrodes 114 and/or 114'. Pulse generator module 104 may be configured to generate electrical stimulation pulses and deliver the electrical stimulation pulses to tissues of a patient via one or more of the electrodes 114 and/or 114' in order to effectuate one or more electrical stimulation therapies. Electrical stimulation pulses as used herein are meant to encompass any electrical signals that may be delivered to tissue of a patient for purposes of treatment of any type of disease or abnormality. For example, when used to treat heart disease, the pulse generator module 104 may generate electrical stimulation pacing pulses for capturing the heart of the patient, i.e. causing the heart to contract in response to the delivered electrical stimulation pulse. In some of these cases, LCP 100 may vary the rate at which pulse generator 104 generates the electrical stimulation pulses, for example in rate responsive pacing. In other embodiments, the electrical stimulation pulses may include defibrillation/cardioversion pulses for shocking the heart out of fibrillation or into a normal heart rhythm. In yet other embodiments, the electrical stimulation pulses may include anti-tachycardia pacing (ATP) pulses. It should be understood that these are just some examples. When used to treat other ailments, the pulse generator module 104 may generate electrical stimulation pulses suitable for neurostimulation therapy or the like. Pulse generator module 104 may include one or more capacitor elements and/or other charge storage devices to aid in generating and delivering appropriate electrical stimulation pulses. In at least some embodiments, pulse generator module 104 may use energy stored in energy storage module 112 to generate the electrical stimulation pulses. In some particular embodiments, pulse generator module 104 may include a switching circuit that is connected to energy storage module 112 and may connect energy storage module 112 to one or more of electrodes 114/114' to generate electrical stimulation pulses.

LCP 100 may further include an electrical sensing module 106 and mechanical sensing module 108. Electrical sensing module 106 may be configured to sense intrinsic cardiac electrical signals conducted from electrodes 114 and/or 114' to electrical sensing module 106. For example, electrical sensing module 106 may be electrically connected to one or more electrodes 114 and/or 114' and electrical sensing module 106 may be configured to receive cardiac electrical signals conducted through electrodes 114 and/or 114' via a sensor amplifier or the like. In some embodiments, the cardiac electrical signals may represent local information from the chamber in which LCP 100 is implanted. For instance, if LCP 100 is implanted within a ventricle of the heart, cardiac electrical signals sensed by LCP 100 through electrodes 114 and/or 114' may represent ventricular cardiac electrical signals. Mechanical sensing module 108 may include, or be electrically connected to, various sensors, such as accelerometers, including multi-axis accelerometers such as two- or three-axis accelerometers, gyroscopes, including multi-axis gyroscopes such as two- or three-axis gyroscopes, blood pressure sensors, heart sound sensors, piezoelectric sensors, blood-oxygen sensors, and/or other sensors which measure one or more physiological parameters of the heart and/or patient. Mechanical sensing module 108, when present, may gather signals from the sensors indicative of the various physiological parameters. Both electrical sensing module 106 and mechanical sensing module 108 may be connected to processing module 110 and may provide signals representative of the sensed cardiac electrical signals and/or physiological signals to processing module 110. Although described with respect to FIG. 1 as separate sensing modules, in some embodiments, electrical sensing module 106 and mechanical sensing module 108 may be combined into a single module. In at least some examples, LCP 100 may only include one of electrical sensing module 106 and mechanical sensing module 108. In some cases, any combination of the processing module 110, electrical sensing module 106, mechanical sensing module 108, communication module 102, pulse generator module 104 and/or energy storage module may be considered a controller of the LCP 100.

Processing module 110 may be configured to direct the operation of LCP 100 and may, in some embodiments, be termed a controller. For example, processing module 110 may be configured to receive cardiac electrical signals from electrical sensing module 106 and/or physiological signals from mechanical sensing module 108. Based on the received signals, processing module 110 may determine, for example, occurrences and types of arrhythmias and other determinations such as whether LCP 100 has become dislodged. Processing module 110 may further receive information from communication module 102. In some embodiments, processing module 110 may additionally use such received information to determine occurrences and types of arrhythmias and/or and other determinations such as whether LCP 100 has become dislodged. In still some additional embodiments, LCP 100 may use the received information instead of the signals received from electrical sensing module 106 and/or mechanical sensing module 108—for instance if the received information is deemed to be more accurate than the signals received from electrical sensing module 106 and/or mechanical sensing module 108 or if electrical sensing module 106 and/or mechanical sensing module 108 have been disabled or omitted from LCP 100.

After determining an occurrence of an arrhythmia, processing module 110 may control pulse generator module 104 to generate electrical stimulation pulses in accordance with one or more electrical stimulation therapies to treat the determined arrhythmia. For example, processing module 110 may control pulse generator module 104 to generate pacing pulses with varying parameters and in different sequences to effectuate one or more electrical stimulation therapies. As one example, in controlling pulse generator module 104 to deliver bradycardia pacing therapy, processing module 110 may control pulse generator module 104 to deliver pacing pulses designed to capture the heart of the patient at a regular interval to help prevent the heart of a patient from falling below a predetermined threshold. In some cases, the rate of pacing may be increased with an increased activity level of the patient (e.g. rate responsive pacing). For instance, processing module 110 may monitor one or more physiological parameters of the patient which may indicate a need for an increased heart rate (e.g. due to increased metabolic demand). Processing module 110 may then increase the rate at which pulse generator 104 generates electrical stimulation pulses.

For ATP therapy, processing module 110 may control pulse generator module 104 to deliver pacing pulses at a rate faster than an intrinsic heart rate of a patient in attempt to force the heart to beat in response to the delivered pacing pulses rather than in response to intrinsic cardiac electrical signals. Once the heart is following the pacing pulses, processing module 110 may control pulse generator module 104 to reduce the rate of delivered pacing pulses down to a safer level. In CRT, processing module 110 may control pulse generator module 104 to deliver pacing pulses in coordination with another device to cause the heart to contract more efficiently. In cases where pulse generator module 104 is capable of generating defibrillation and/or cardioversion pulses for defibrillation/cardioversion therapy, processing module 110 may control pulse generator module 104 to generate such defibrillation and/or cardioversion pulses. In some cases, processing module 110 may control pulse generator module 104 to generate electrical stimulation pulses to provide electrical stimulation therapies different than those examples described above.

Aside from controlling pulse generator module 104 to generate different types of electrical stimulation pulses and in different sequences, in some embodiments, processing module 110 may also control pulse generator module 104 to generate the various electrical stimulation pulses with varying pulse parameters. For example, each electrical stimulation pulse may have a pulse width and a pulse amplitude. Processing module 110 may control pulse generator module 104 to generate the various electrical stimulation pulses with specific pulse widths and pulse amplitudes. For example, processing module 110 may cause pulse generator module 104 to adjust the pulse width and/or the pulse amplitude of electrical stimulation pulses if the electrical stimulation pulses are not effectively capturing the heart. Such control of the specific parameters of the various electrical stimulation pulses may help LCP 100 provide more effective delivery of electrical stimulation therapy.

In some embodiments, processing module 110 may further control communication module 102 to send information to other devices. For example, processing module 110 may control communication module 102 to generate one or more communication signals for communicating with other devices of a system of devices. For instance, processing module 110 may control communication module 102 to generate communication signals in particular pulse sequences, where the specific sequences convey different information. Communication module 102 may also receive communication signals for potential action by processing module 110.

In further embodiments, processing module 110 may control switching circuitry by which communication module 102 and pulse generator module 104 deliver communication signals and/or electrical stimulation pulses to tissue of the patient. As described above, both communication module 102 and pulse generator module 104 may include circuitry for connecting one or more electrodes 114 and/114' to communication module 102 and/or pulse generator module 104 so those modules may deliver the communication signals and electrical stimulation pulses to tissue of the patient. The specific combination of one or more electrodes by which communication module 102 and/or pulse generator module 104 deliver communication signals and electrical stimulation pulses may influence the reception of communication signals and/or the effectiveness of electrical stimulation pulses. Although it was described that each of communication module 102 and pulse generator module 104 may include switching circuitry, in some embodiments, LCP 100 may have a single switching module connected to the communication module 102, the pulse generator module 104, and electrodes 114 and/or 114'. In such embodiments, processing module 110 may control the switching module to connect modules 102/104 and electrodes 114/114' as appropriate.

In some embodiments, processing module 110 may include a pre-programmed chip, such as a very-large-scale integration (VLSI) chip or an application specific integrated circuit (ASIC). In such embodiments, the chip may be pre-programmed with control logic in order to control the operation of LCP 100. By using a pre-programmed chip, processing module 110 may use less power than other programmable circuits while able to maintain basic functionality, thereby potentially increasing the battery life of LCP 100. In other instances, processing module 110 may include a programmable microprocessor or the like. Such a programmable microprocessor may allow a user to adjust the control logic of LCP 100 after manufacture, thereby allowing for greater flexibility of LCP 100 than when using a pre-programmed chip. In still other embodiments, processing module 110 may not be a single component. For example, processing module 110 may include multiple components positioned at disparate locations within LCP 100 in order to perform the various described functions. For example, certain functions may be performed in one component of processing module 110, while other functions are performed in a separate component of processing module 110.

Processing module 110, in additional embodiments, may include a memory circuit and processing module 110 may store information on and read information from the memory circuit. In other embodiments, LCP 100 may include a separate memory circuit (not shown) that is in communication with processing module 110, such that processing module 110 may read and write information to and from the separate memory circuit. The memory circuit, whether part of processing module 110 or separate from processing module 110, may be volatile memory, non-volatile memory, or a combination of volatile memory and non-volatile memory.

Energy storage module 112 may provide a power source to LCP 100 for its operations. In some embodiments, energy storage module 112 may be a non-rechargeable lithium-based battery. In other embodiments, the non-rechargeable battery may be made from other suitable materials. In some embodiments, energy storage module 112 may include a rechargeable battery. In still other embodiments, energy storage module 112 may include other types of energy storage devices such as capacitors or super capacitors.

To implant LCP 100 inside a patient's body, an operator (e.g., a physician, clinician, etc.), may fix LCP 100 to the cardiac tissue of the patient's heart. To facilitate fixation, LCP 100 may include one or more anchors 116. The one or more anchors 116 are shown schematically in FIG. 1. The one or more anchors 116 may include any number of fixation or anchoring mechanisms. For example, one or more anchors 116 may include one or more pins, staples, threads, screws, helix, tines, and/or the like. In some embodiments, although not shown, one or more anchors 116 may include threads on its external surface that may run along at least a partial length of an anchor member. The threads may provide friction between the cardiac tissue and the anchor to help fix the anchor member within the cardiac tissue. In some cases, the one or more anchors 116 may include an anchor member that has a cork-screw shape that can be screwed into the cardiac tissue. In other embodiments, anchor 116 may include other structures such as barbs, spikes, or the like to facilitate engagement with the surrounding cardiac tissue.

In some examples, LCP 100 may be configured to be implanted on a patient's heart or within a chamber of the patient's heart. For instance, LCP 100 may be implanted within any of a left atrium, right atrium, left ventricle, or right ventricle of a patient's heart. By being implanted within a specific chamber, LCP 100 may be able to sense cardiac electrical signals originating or emanating from the specific chamber that other devices may not be able to sense with such resolution. Where LCP 100 is configured to be implanted on a patient's heart, LCP 100 may be configured to be implanted on or adjacent to one of the chambers of the heart, or on or adjacent to a path along which intrinsically generated cardiac electrical signals generally follow. In these examples, LCP 100 may also have an enhanced ability to sense localized intrinsic cardiac electrical signals and deliver localized electrical stimulation therapy.

Figure 2:
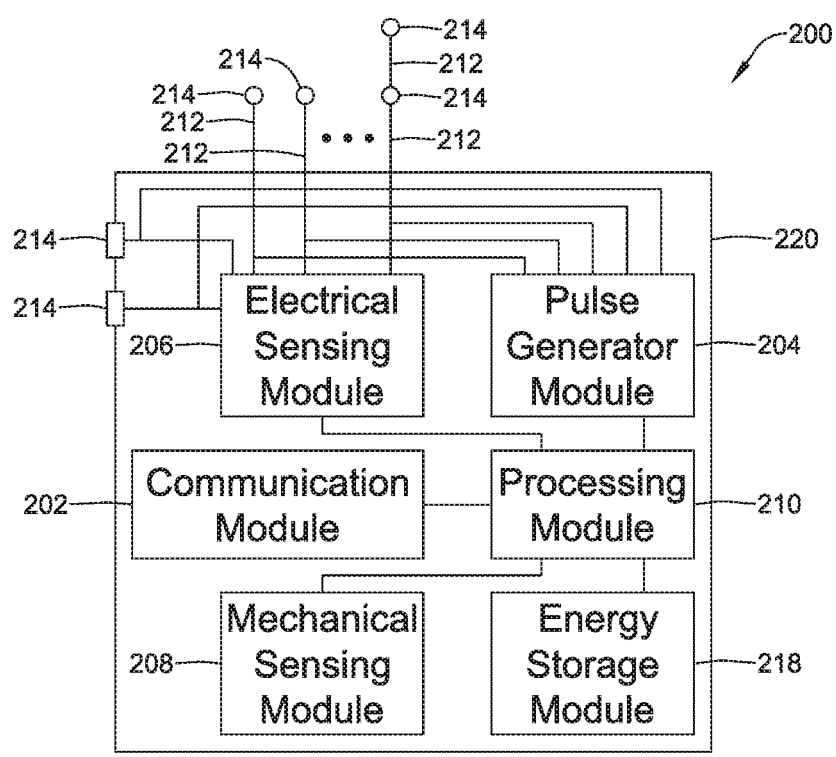
FIG. 2 is a schematic block diagram of another illustrative medical device that may be used in conjunction with the LCP of FIG. 1.

FIG. 2 depicts an embodiment of another device, medical device (MD) 200, which may operate to sense physiological signals and parameters and deliver one or more types of electrical stimulation therapy to tissues of the patient. In the embodiment shown, MD 200 may include a communication module 202, a pulse generator module 204, an electrical sensing module 206, a mechanical sensing module 208, a processing module 210, and an energy storage module 218. Each of modules 202, 204, 206, 208, and 210 may be similar to modules 102, 104, 106, 108, and 110 of LCP 100. Additionally, energy storage module 218 may be similar to energy storage module 112 of LCP 100. However, in some embodiments, MD 200 may have a larger volume within housing 220. In such embodiments, MD 200 may include a larger energy storage module 218 and/or a larger processing module 210 capable of handling more complex operations than processing module 110 of LCP 100.

While MD 200 may be another leadless device such as shown in FIG. 1, in some instances MD 200 may include leads, such as leads 212. Leads 212 may include electrical wires that conduct electrical signals between electrodes 214 and one or more modules located within housing 220. In some cases, leads 212 may be connected to and extend away from housing 220 of MD 200. In some embodiments, leads 212 are implanted on, within, or adjacent to a heart of a patient. Leads 212 may contain one or more electrodes 214 positioned at various locations on leads 212 and various distances from housing 220. Some leads 212 may only include a single electrode 214, while other leads 212 may include multiple electrodes 214. Generally, electrodes 214 are positioned on leads 212 such that when leads 212 are implanted within the patient, one or more of the electrodes 214 are positioned to perform a desired function. In some cases, the one or more of the electrodes 214 may be in contact with the patient's cardiac tissue. In other cases, the one or more of the electrodes 214 may be positioned subcutaneously but adjacent the patient's heart. The electrodes 214 may conduct intrinsically generated electrical cardiac signals to leads 212. Leads 212 may, in turn, conduct the received electrical cardiac signals to one or more of the modules 202, 204, 206, and 208 of MD 200. In some cases, MD 200 may generate electrical stimulation signals, and leads 212 may conduct the generated electrical stimulation signals to electrodes 214. Electrodes 214 may then conduct the electrical stimulation signals to the cardiac tissue of the patient (either directly or indirectly). MD 200 may also include one or more electrodes 214 not disposed on a lead 212. For example, one or more electrodes 214 may be connected directly to housing 220.

Leads 212, in some embodiments, may additionally contain one or more sensors, such as accelerometers, blood pressure sensors, heart sound sensors, blood-oxygen sensors, and/or other sensors which are configured to measure one or more physiological parameters of the heart and/or patient. In such embodiments, mechanical sensing module 208 may be in electrical communication with leads 212 and may receive signals generated from such sensors.

While not required, in some embodiments MD 200 may be an implantable medical device. In such embodiments, housing 220 of MD 200 may be implanted in, for example, a transthoracic region of the patient. Housing 220 may generally include any of a number of known materials that are safe for implantation in a human body and may, when implanted, hermetically seal the various components of MD 200 from fluids and tissues of the patient's body. In such embodiments, leads 212 may be implanted at one or more various locations within the patient, such as within the heart of the patient, adjacent to the heart of the patient, adjacent to the spine of the patient, or any other desired location.

In some embodiments, MD 200 may be an implantable cardiac pacemaker (ICP). In these embodiments, MD 200 may have one or more leads, for example leads 212, which are implanted on or within the patient's heart. The one or more leads 212 may include one or more electrodes 214 that are in contact with cardiac tissue and/or blood of the patient's heart. MD 200 may be configured to sense intrinsically generated cardiac electrical signals and determine, for example, one or more cardiac arrhythmias based on analysis of the sensed signals. MD 200 may be configured to deliver CRT, ATP therapy, bradycardia therapy, and/or other therapy types via leads 212 implanted within the heart. In some embodiments, MD 200 may additionally be configured to provide defibrillation/cardioversion therapy.

In some instances, MD 200 may be an implantable cardioverter-defibrillator (ICD). In such embodiments, MD 200 may include one or more leads implanted within a patient's heart. MD 200 may also be configured to sense electrical cardiac signals, determine occurrences of tachyarrhythmias based on the sensed electrical cardiac signals, and deliver defibrillation and/or cardioversion therapy in response to determining an occurrence of a tachyarrhythmia (for example by delivering defibrillation and/or cardioversion pulses to the heart of the patient). In other embodiments, MD 200 may be a subcutaneous implantable cardioverter-defibrillator (SICD). In embodiments where MD 200 is an SICD, one of leads 212 may be a subcutaneously implanted lead. In at least some embodiments where MD 200 is an SICD, MD 200 may include only a single lead which is implanted subcutaneously but outside of the chest cavity, however this is not required.

In some embodiments, MD 200 may not be an implantable medical device. Rather, MD 200 may be a device external to the patient's body, and electrodes 214 may be skin-electrodes that are placed on a patient's body. In such embodiments, MD 200 may be able to sense surface electrical signals (e.g. electrical cardiac signals that are generated by the heart or electrical signals generated by a device implanted within a patient's body and conducted through the body to the skin). MD 200 may further be configured to deliver various types of electrical stimulation therapy, including, for example, defibrillation therapy via skin-electrodes 214.

Figure 3:
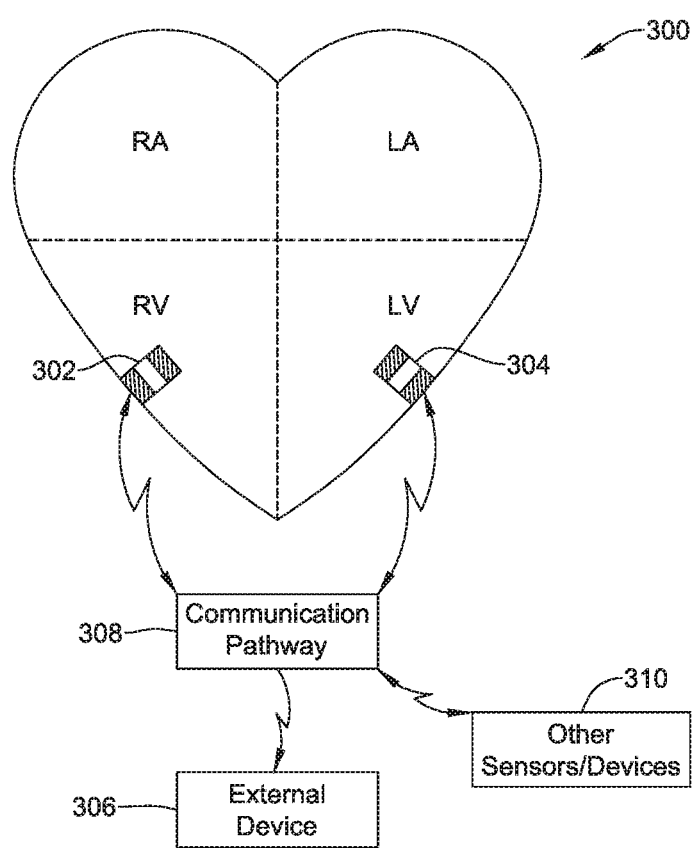
FIG. 3 is a schematic diagram of an exemplary medical system that includes multiple LCPs and/or other devices in communication with one another.

FIG. 3 illustrates an embodiment of a medical device system and a communication pathway through which multiple medical devices 302, 304, 306, and/or 310 of the medical device system may communicate. In the embodiment shown, medical device system 300 may include LCPs 302 and 304, external medical device 306, and other sensors/devices 310. External device 306 may be a device disposed external to a patient's body, as described previously with respect to MD 200. In at least some examples, external device 306 may represent an external support device such as a device programmer, as will be described in more detail below. Other sensors/devices 310 may be any of the devices described previously with respect to MD 200, such as ICPs, ICDs, and SICDs. Other sensors/devices 310 may also include various diagnostic sensors that gather information about the patient, such as accelerometers, blood pressure sensors, or the like. In some cases, other sensors/devices 310 may include an external programmer device that may be used to program one or more devices of system 300.

Various devices of system 300 may communicate via communication pathway 308. For example, LCPs 302 and/or 304 may sense intrinsic cardiac electrical signals and may communicate such signals to one or more other devices 302/304, 306, and 310 of system 300 via communication pathway 308. In one embodiment, one or more of devices 302/304 may receive such signals and, based on the received signals, determine an occurrence of an arrhythmia. In some cases, device or devices 302/304 may communicate such determinations to one or more other devices 306 and 310 of system 300. In some cases, one or more of devices 302/304, 306, and 310 of system 300 may take action based on the communicated determination of an arrhythmia, such as by delivering a suitable electrical stimulation to the heart of the patient. One or more of devices 302/304, 306, and 310 of system 300 may additionally communicate command or response messages via communication pathway 308. The command messages may cause a receiving device to take a particular action whereas response messages may include requested information or a confirmation that a receiving device did, in fact, receive a communicated message or data.

It is contemplated that the various devices of system 300 may communicate via pathway 308 using RF signals, inductive coupling, optical signals, acoustic signals, or any other signals suitable for communication. Additionally, in at least some embodiments, the various devices of system 300 may communicate via pathway 308 using multiple signal types. For instance, other sensors/device 310 may communicate with external device 306 using a first signal type (e.g. RF communication) but communicate with LCPs 302/304 using a second signal type (e.g. conducted communication). Further, in some embodiments, communication between devices may be limited. For instance, as described above, in some embodiments, LCPs 302/304 may communicate with external device 306 only through other sensors/devices 310, where LCPs 302/304 send signals to other sensors/devices 310, and other sensors/devices 310 relay the received signals to external device 306.

In some cases, the various devices of system 300 may communicate via pathway 308 using conducted communication signals. Accordingly, devices of system 300 may have components that allow for such conducted communication. For instance, the devices of system 300 may be configured to transmit conducted communication signals (e.g. a voltage and/or current waveform punctuated with current and/or voltage pulses, referred herein as electrical communication pulses) into the patient's body via one or more electrodes of a transmitting device, and may receive the conducted communication signals via one or more electrodes of a receiving device. The patient's body may "conduct" the conducted communication signals from the one or more electrodes of the transmitting device to the electrodes of the receiving device in the system 300. In such embodiments, the delivered conducted communication signals may differ from pacing pulses, defibrillation and/or cardioversion pulses, or other electrical stimulation therapy signals. For example, the devices of system 300 may deliver electrical communication pulses at an amplitude/pulse width that is sub-threshold. That is, the communication pulses have an amplitude/pulse width designed to not capture the heart. In some cases, the amplitude/pulse width of the delivered electrical communication pulses may be above the capture threshold of the heart, but may be delivered during a refractory period of the heart and/or may be incorporated in or modulated onto a pacing pulse, if desired.

Additionally, unlike normal electrical stimulation therapy pulses, the electrical communication pulses may be delivered in specific sequences which convey information to receiving devices. For instance, delivered electrical communication pulses may be modulated in any suitable manner to encode communicated information. In some cases, the communication pulses may be pulse width modulated and/or amplitude modulated. Alternatively, or in addition, the time between pulses may be modulated to encode desired information. In some cases, a predefined sequence of communication pulses may represent a corresponding symbol (e.g. a logic "1" symbol, a logic "0" symbol, an ATP therapy trigger symbol, etc.). In some cases, conducted communication pulses may be voltage pulses, current pulses, biphasic voltage pulses, biphasic current pulses, or any other suitable electrical pulse as desired.

Figure 4:
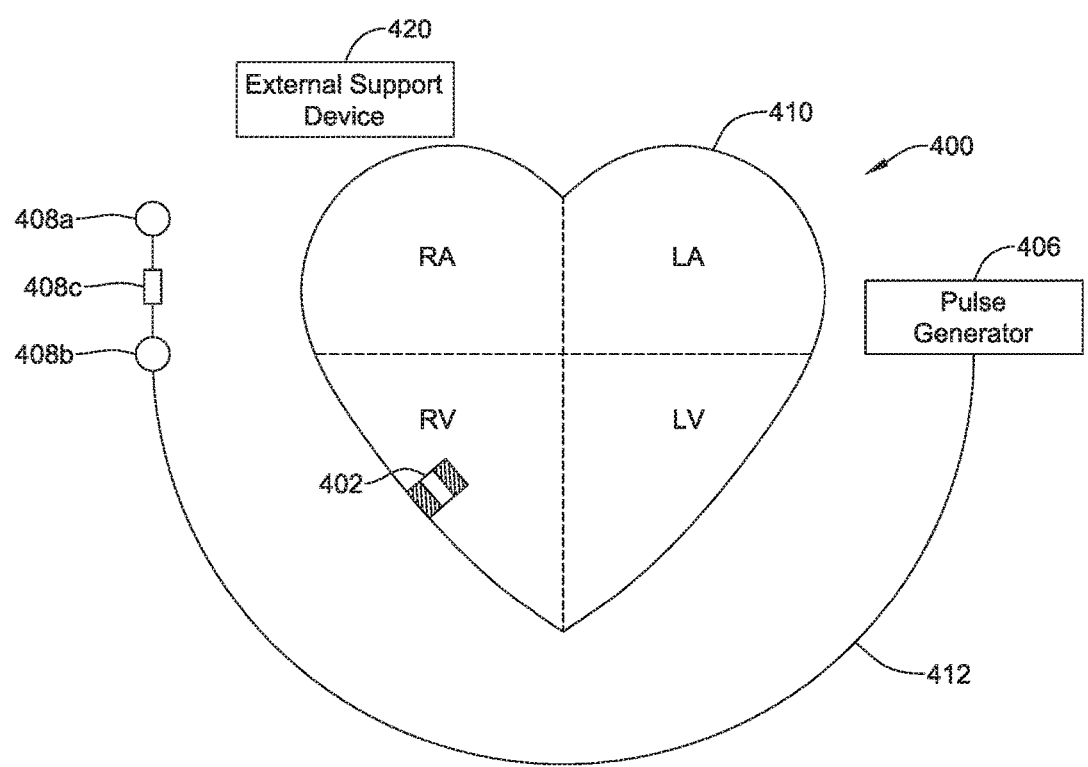
FIG. 4 is a schematic diagram of a system including an LCP and another medical device, in accordance with another embodiment of the present disclosure.

FIG. 4 depicts an illustrative medical device system 400 that may be configured to operate together. For example, system 400 may include multiple devices that are implanted within a patient and are configured to sense physiological signals, determine occurrences of cardiac arrhythmias, and deliver electrical stimulation to treat detected cardiac arrhythmias. In some embodiments, the devices of system 400 may be configured to determine occurrences of dislodgment of one or more devices of system 400. In FIG. 4, an LCP 402 is shown fixed to the interior of the right ventricle of the heart 410, and a pulse generator 406 is shown coupled to a lead 412 having one or more electrodes 408a-408c. In some cases, pulse generator 406 may be part of a subcutaneous implantable cardioverter-defibrillator (SICD), and the one or more electrodes 408a-408c may be positioned subcutaneously adjacent the heart. LCP 402 may communicate with the SICD, such as via communication pathway 308. The locations of LCP 402, pulse generator 406, lead 412, and electrodes 408a-c depicted in FIG. 4 are just exemplary. In other embodiments of system 400, LCP 402 may be positioned in the left ventricle, right atrium, or left atrium of the heart, as desired. In still other embodiments, LCP 402 may be implanted externally adjacent to heart 410 or even remote from heart 410.

Medical device system 400 may also include external support device 420. External support device 420 can be used to perform functions such as device identification, device programming and/or transfer of real-time and/or stored data between devices using one or more of the communication techniques described herein, or other functions involving communication with one or more devices of system 400. As one example, communication between external support device 420 and pulse generator 406 can be performed via a wireless mode, and communication between pulse generator 406 and LCP 402 can be performed via a conducted communication mode. In some embodiments, communication between LCP 402 and external support device 420 is accomplished by sending communication information through pulse generator 406. However, in other embodiments, communication between the LCP 402 and external support device 420 may be via a communication module.

FIG. 4 only illustrates one example embodiment of a medical device system that may be configured to operate according to techniques disclosed herein. Other example medical device systems may include additional or different medical devices and/or configurations. For instance, other medical device systems that are suitable to operate according to techniques disclosed herein may include additional LCPs implanted within the heart. Another example medical device system may include a plurality of LCPs with or without other devices such as pulse generator 406, with at least one LCP capable of delivering defibrillation therapy. Still another example may include one or more LCPs implanted along with a transvenous pacemaker and with or without an implanted SICD. In yet other embodiments, the configuration or placement of the medical devices, leads, and/or electrodes may be different from those depicted in FIG. 4. Accordingly, it should be recognized that numerous other medical device systems, different from system 400 depicted in FIG. 4, may be operated in accordance with techniques disclosed herein. As such, the embodiment shown in FIG. 4 should not be viewed as limiting in any way.

As mentioned LCP 100 and/or MD 200 may be configured to deliver electrical stimulation therapy to a heart of a patient. For instance, LCP 100 and/or MD 200 may be configured to generate pacing pulses and deliver those pacing pulses to the heart of the patient in order to pace the heart. Additionally, LCP 100 and/or MD 200 may be configured to adjust the rate of pacing pulse generation and delivery in a rate responsive manner in order to increase or decrease the cardiac output based on determined factors relating to metabolic demand. In some cases, it may be beneficial to limit the amount of time LCP 100 and/or MD 200 generate and deliver pacing pulses above a certain pacing rate in order to reduce a stress level of the heart and give the heart a chance to rest.

Figure 5:
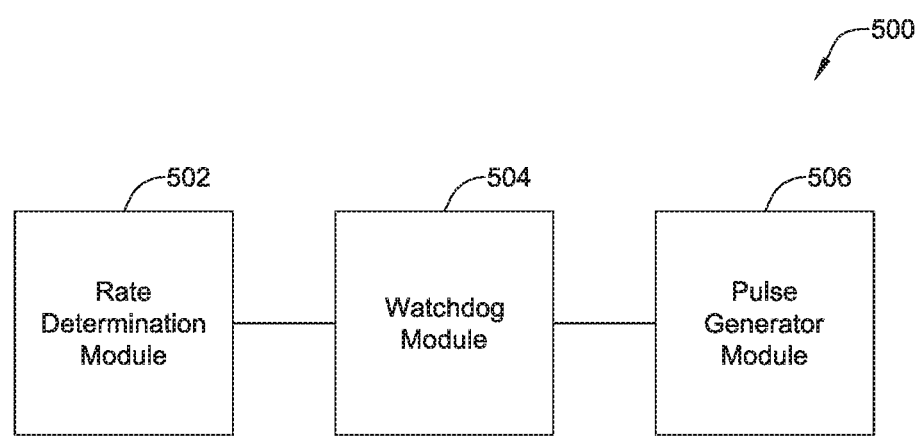
FIG. 5 is block diagram of an example of a controller circuit for implementing a watchdog function, according to one aspect of the present disclosure.

FIG. 5 depicts an example controller circuit 500 of a medical device, such as LCP 100 or MD 200. The illustrative controller circuit 500 includes rate determination module (RDM) 502 connected to watchdog module 504. Watchdog module 504 is further connected to pulse generator module 506.

In some embodiments, controller circuit 500 may be part of a medical device that is configured to deliver pacing pulses to a heart of a patient in order to control a heart rate. The medical device may be further configured to deliver the pacing pulses in a rate responsive manner, increasing or decreasing the rate of delivery of pacing pulses based on one or more sensed signals and/or determined metrics. For instance, RDM 502 may represent a circuit that outputs a current pacing rate. RDM 502 may receive one or more signals sensed from one or more sensors and/or determine one or more metrics based on the received signals. Some example signals that RDM 502 may receive and/or use in determining a current pacing rate may include transthoracic impedance, temperature, and accelerometer signals. Some example parameters that RDM 502 may determine based on such signal(s) include a respiration rate (using transthoracic impedance signal), a blood temperature (using the blood temperature signal), and an activity level and/or posture of the patient (using the accelerometer signal). Of course, in other embodiments, a different circuit (e.g. SICD) can receive these or other signals and/or determine such parameters and then communicate the signals and/or parameters to RDM 502.

Using the received signals and/or determined parameters, RDM 502 may determine a current pacing rate. The received signals and/or determined parameters may represent measures of metabolic demand of the patient. For example, an elevated respiration rate, an elevated blood temperature, and/or an elevated activity level, all in comparison to individual baseline levels, may indicate that the patient needs increased cardiac output, which can be achieved by an increased pacing rate. In additional, or alternative embodiments, certain chemical markers or levels, body position, and/or pacing rate of another implanted device may all further be measures of metabolic demand. LCP 100 may sense any number or all of these measures, or may receive indications of these measures from another device in order for RDM 502 to determine a pacing rate.

However, in still other embodiments, LCP 100 may not be the device that determines a pacing rate. For instance, another device may sense one or more measures related to metabolic demand, or receive such measures from still another device, and determine a pacing rate based on the sensed or received measures. In these embodiments, this other device may then communicate the pacing rate to LCP 100, which uses the received pacing rate in conjunction with the presently disclosed watchdog techniques to deliver pacing pulses to the heart.

In some embodiments, RDM 502 may determine a pacing rate based on only one of these measures of metabolic demand. Alternatively, RDM 502 may determine a pacing rate based individually on each of two or more of these measures of metabolic demand, and determine the current pacing rate as the highest pacing rate determined based on the individual measures. Alternatively, RDM 502 may blend each of the individual measures into an overall measure of metabolic demand and determined the current pacing rate based on the overall measure.

RDM 502 may additionally enforce a lower rate limit (LRL), representing a minimum pacing rate. Regardless of the measures of metabolic demand, the LRL may be the lowest rate at which the medical device is configured to deliver pacing pulses in order to ensure a safe base level of cardiac output for the patient.

Figure 6:
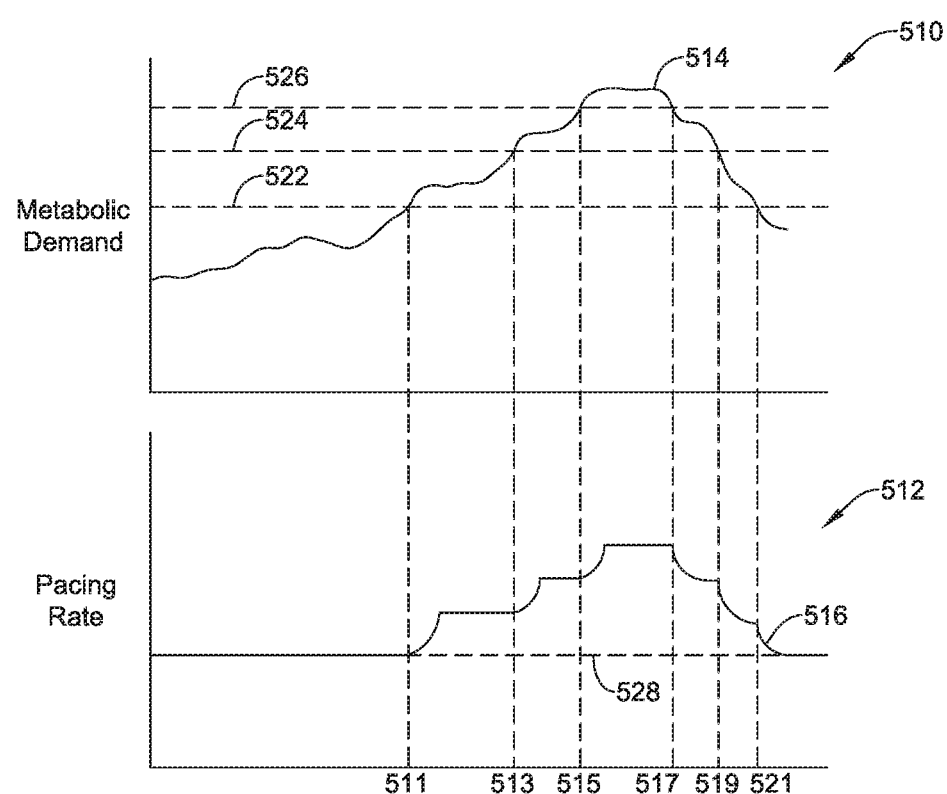
FIG. 6 depicts a graph of an illustrative metabolic demand of a patient and a graph of a corresponding pacing rate.

Accordingly, RDM 502 may vary the current pacing rate over time based on one or more measures of metabolic demand, such as depicted in the example shown in FIG. 6. FIG. 6 depicts a graph 510 of metabolic demand 514 versus time along with a graph 512 of a current pacing rate 516 as generated by RDM 502. In some embodiments, the medical device may use thresholding to determine the current pacing rate based on the sensed or determined metabolic demand 514. For instance, the medical device may have three thresholds, thresholds 522, 524, and 526 which may represent different levels of metabolic demand, and which may drive changes in the current pacing rate 516. As can be seen in FIG. 6, threshold 528 of current pacing rate 516 may represent an LRL, and the medical device may not output a current pacing rate lower than the LRL. Accordingly, where metabolic demand 514 is below demand threshold 522, the medical device may maintain the current pacing rate at the LRL. Once metabolic demand 514 crosses demand threshold 522, the medical device may determine that there is a need for increased cardiac output and may thus increase the current pacing rate 516, as can be seen between times 511 and 513. Additionally, as metabolic demand 514 crosses demand thresholds 524 and 526, the medical device may again increase the current pacing rate 516, as seen between times 513, 515 and between times 515, 517. Further, as metabolic demand drops below demand thresholds 526, 524, and 522, the medical device may decrease the current pacing rate 516, as seen between times 517, 519, between times 519, 521, and after time 521.

It should be understood that FIG. 6 shows only one example by which the medical device may adjust the pacing rate over time. For instance, the medical device may use a continuous function based on metabolic demand 514 to determine the current pacing rate 516, rather than the thresholding approach shown in FIG. 6. Additionally, although FIG. 6 depicts the current pacing rate 516 transitioning over time between pacing rates, in other embodiments the current pacing rate 516 may be abruptly changed between different pacing rates if desired.

As RDM 502 determines the current pacing rate, RDM 502 may communicate the current pacing rate to watchdog module 504 (see FIG. 5). In general, watchdog module 504 may be configured to monitor the received current pacing rate and determine when the current pacing rate is elevated above a baseline pacing rate like the LRL. Watchdog module 504 may be further configured to prevent the current pacing rate from staying at an elevated rate for a prolonged period of time, as this may cause undue stress on the heart.

In order to determine a relative stress level of the heart and to determine when the current pacing rate has been at an elevated rate for too long a period of time, watchdog module 504 may be configured to determine a heart stress tracking value (HSTV). In at least some embodiments, which will be discussed in more detail below, the HSTV may be dependent at least in part on the current pacing rate.

Watchdog module 504 may be implemented with a base pacing rate. In some embodiments, the base pacing rate may be the LRL. However, in other embodiments, the base pacing rate may be higher than the base pacing rate. As some examples, the LRL may be set at around 60 pulses per minute (could be patient dependent). In embodiments where the base pacing rate is higher than the LRL, the base pacing rate may be set at about 65 pulses per minute or 70 pulses per minute. However, these are just some examples. This may allow some variation in the pacing rate without trigging the watchdog feature.

Watchdog module 504 may determine when the current pacing rate is equal to or above the base pacing rate, indicating that the current pacing rate is at an elevated pacing rate. Once watchdog module 504 determines that the current pacing rate is at an elevated pacing rate, watchdog module 504 may begin to modify the HSTV. While the current pacing rate stays above the base pacing rate, watchdog module 504 may continue to modify the HSTV and determine if and when the HSTV crosses an HSTV threshold. When the HSTV crosses the HSTV threshold, watchdog module 504 may be configured to change the current pacing rate to a rest pacing rate, and maintain the current pacing at the rest pacing rate for a predetermined period of time. Examples of these operations will be described in more detail below.

One example HSTV that watchdog module 504 may implement is a simple counter that may count up or count down in a monotonic fashion. In these embodiments, once watchdog module 504 determines that the current pacing rate is at or above the base pacing rate, watchdog module 504 may begin counting up or counting down, depending on the implementation. For instance, watchdog module 504 may include a clock, or use a clock signal from another portion of the medical device. Once every clock cycle, watchdog module 504 may increment or decrement a counter. When the counter reaches a predetermined threshold, watchdog module 504 may implement the rest pacing rate. When the watchdog module 504 is incrementing a counter from zero, the predetermined threshold may be some positive value. Where watchdog module 504 is decrementing a counter, the initial value may be a positive value and the predetermined threshold may be zero. In some cases, it is contemplated that the positive value may be programmable in either implantation.

Figure 7:
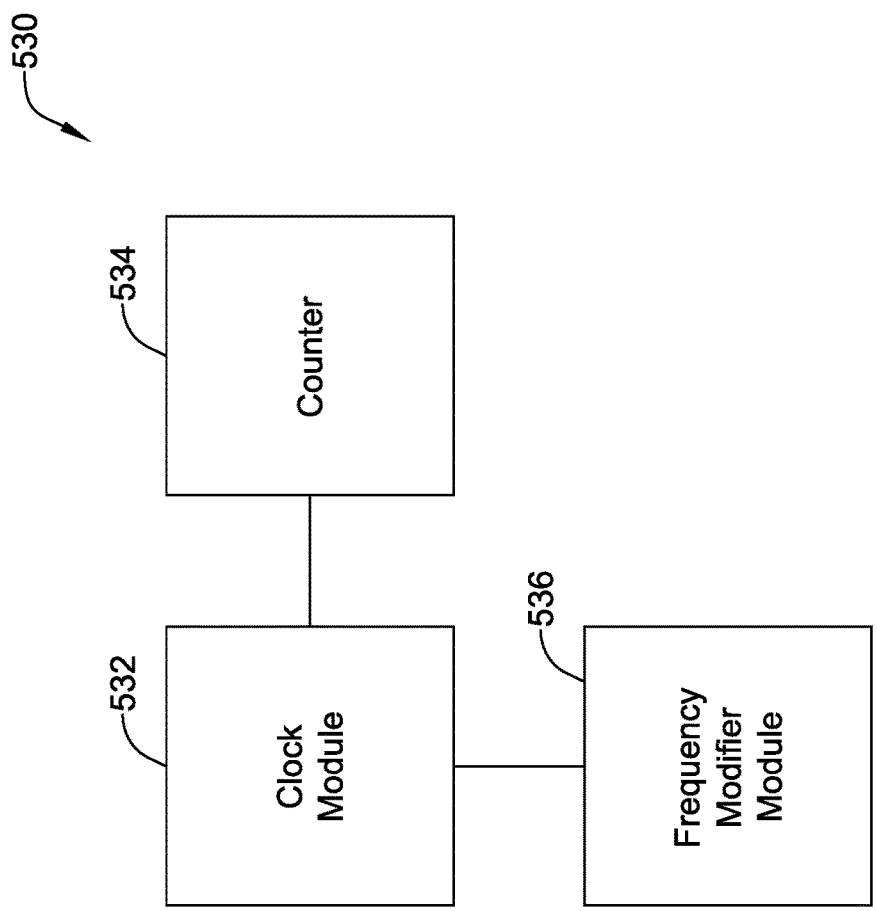
FIG. 7 is block diagram of an illustrative circuit for incrementing a counter at different rates.

In some instances, the rate at which watchdog module 504 increments or decrements the counter may be dependent at least in part on the pacing rate. For example, FIG. 7 depicts an illustrative circuit 530 that may be included in watchdog module 504. Circuit 530 includes a clock module 532, a counter 534, and a frequency modifier module 536. Clock module 532 may function similarly to clocks in other electrical devices by operating at a particular frequency to drive operation of the device or circuit. Counter 534, when the current pacing rate is equal to or above the base pacing rate, may increment or decrement the counter (e.g. an HSTV value) each clock cycle as determined by the operating frequency of clock module 532.

Figure 8:
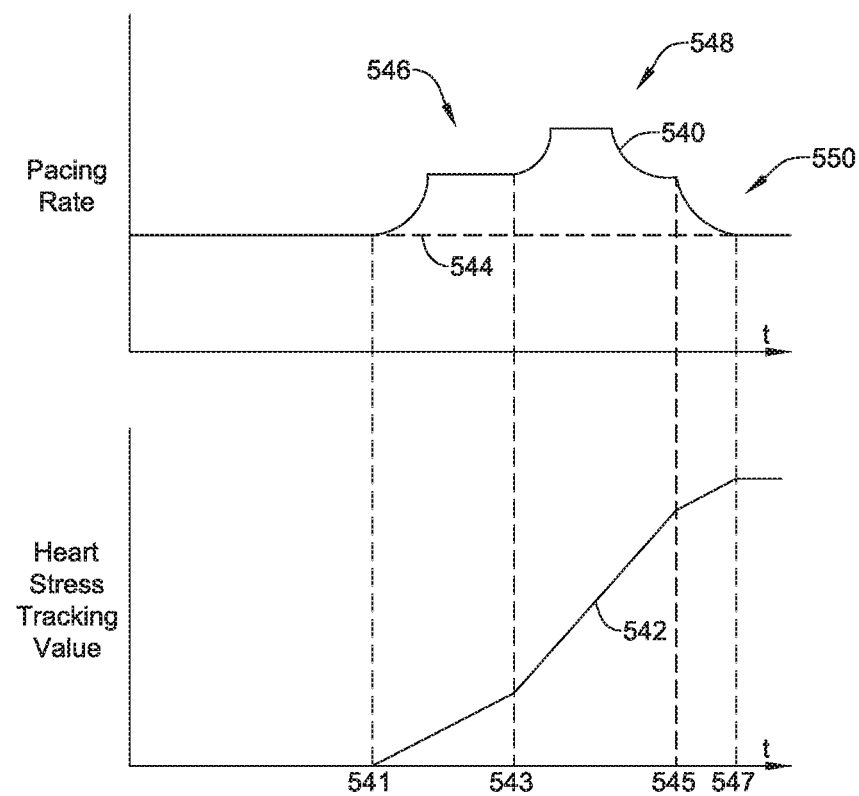
FIG. 8 depicts a graph of a current pacing rate versus time and a corresponding graph of how a heart stress tracking value may modified based on the current pacing rate, in accordance with aspects of the present disclosure.

Frequency modifier module 536 may be configured to modify the frequency of clock module 532 based on the current pacing rate. FIG. 8 illustrates one example implementation of how frequency modifier module 536 may operate. FIG. 8 depicts a current pacing rate 540 versus time along with a corresponding HSTV 542. In the example of FIG. 8, the base pacing rate may be equal to LRL 544. For instance, once current pacing rate 540 increases above LRL 544, such as at time 541, HSTV 542 begins to increase. As can be seen in FIG. 8, while current pacing rate 540 is at or below a first value and above LRL 544, as in region 546 between time 541 and 543, HSTV 542 increases at a first rate. Once current pacing rate 540 increases above the first value, such as at time 543, and while current pacing rate 540 is within in region 548 between times 543 and 545, HSTV 542 increases at a second rate that is greater than the first rate. Additionally, as seen in FIG. 8, when current pacing rate 540 falls back below the first value, such as at time 545, HSTV 542 may return to increasing at the first rate. HSTV 542 may maintain this first rate while current pacing rate 540 is between LRL 544 and the first value, such as between times 545 and 547. After time 547, where current pacing rate 540 falls back to LRL 544, HSTV 542 may simply maintain its value.

The increase in the rate of increase of HSTV 542 while current pacing rate 540 is above the first value may be effectuated by frequency modifier module 536. For instance, frequency modifier module 536 may modify the frequency of operation of clock module 532, such as by increasing the frequency. Accordingly, this increased frequency of operation of clock module 532 also increases the rate at which counter 534 increments a counter value (e.g. an HSTV value)—thereby increasing HSTV 542 at a faster rate. In some embodiments, frequency modifier module 536 may double the frequency. Additionally, other embodiments may have additional threshold levels where frequency modifier module 536 modifies the frequency. For example, some embodiments may implement another threshold level above the first value of FIG. 8 where frequency modifier module 536 again increases the frequency of operation of clock module 532. In some of these embodiments, frequency modifier module 536 may again double the frequency of operation. However, it should be understood these are only examples. In general, frequency modifier module 536 may be configured to modify the frequency of operation of clock module 532 in any manner using any amount of thresholds or on a continuous basis.

Another implementation of an HSTV may be a heartbeat or pacing pulse counter. For instance, once current pacing rate 540 increases above the base pacing rate, and while current pace rate 540 stays above the base pacing rate, watchdog module 504 may begin counting each heart beat or delivered pacing pulse. In some instances, watchdog module 504 may receive detected heart beats from another portion of the medical device that is directly connected to electrodes of the medical device and that is able to sense cardiac electrical signals. Alternatively, watchdog module 504 may receive an indication when a pacing pulse is generated. In these embodiments, watchdog module 504 may count the heartbeats or the pacing pulses in a counter and compare the counter to a heartbeat or pacing pulse threshold (e.g. HSTV threshold). Once the counter reaches the threshold, watchdog module 504 may modify the current pacing rate to be the rest pacing rate. In these embodiments, as the pacing rate increases, the counter naturally begins accumulating faster as more heartbeats occur, or pacing pulses are generated, per minute.

In still other embodiments, watchdog module 504 may determine the integral of pacing rate 540 above the base pacing rate as the HSTV. The integral of the pacing rate 540 may then be compared to an integral threshold value, and if it exceeds the integral threshold value (e.g. HSTV threshold), the watchdog module 504 may modify the current pacing rate to be the rest pacing rate.

Figure 9:
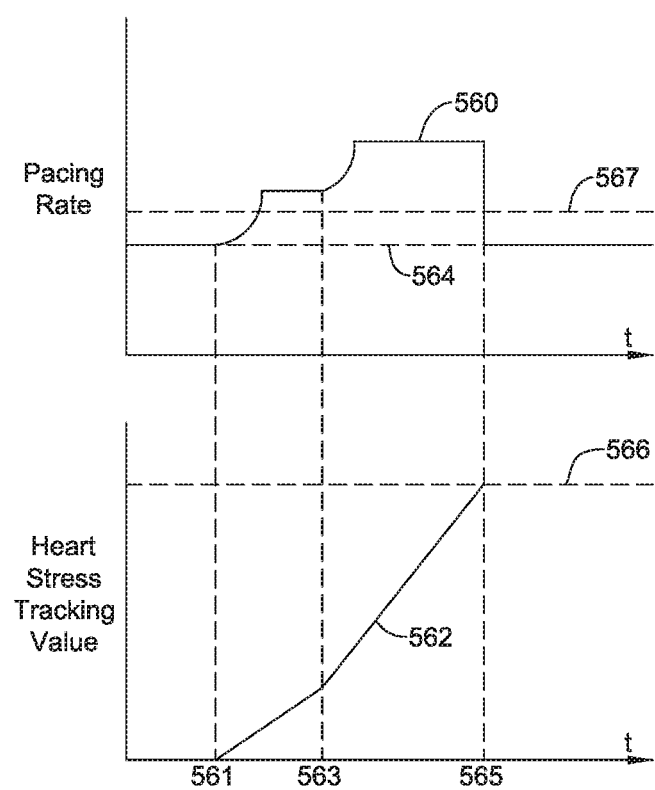
FIG. 9 depicts a graph of a current pacing rate versus time and a corresponding graph of a heart stress tracking value and how the current pacing rate may be modified based on the heart stress tracking value, in accordance with aspects of the present disclosure.

As mentioned, once watchdog module 504 has determined that the HSTV has reached the HSTV threshold, watchdog module 504 may implement a rest pacing period. FIG. 9 illustrates current pacing rate 560 along with HSTV 562 where watchdog module 504 implements a rest pacing period. Similar to FIG. 8, when current pacing rate 560 increase above base pacing rate 564, HSTV 562 may begin to increase at a first rate, for instance at time 561. Also, if current pacing rate 560 increases above a first level, HSTV 562 may increase at a second rate that is greater than the first rate, such as at time 563. While current pacing rate 560 is above base pacing rate 564, watchdog module 504 may be comparing HSTV 562 to an HSTV threshold 566.

While HSTV 562 is below HSTV threshold 566, watchdog module 504 may pass through the current pacing rate 560 to pulse generator module 506. Pulse generator module 506 may be configured to generate pacing pulses at the current pacing rate and to deliver those generated pacing pulses to the heart of the patient.

If and/or when watchdog module 504 determines that HSTV 562 reaches HSTV threshold 566, such as at time 565, watchdog module 504 may implement a rest pacing period. Instead of simply passing through the current pacing rate 560 to the pulse generator module 506, watchdog module 504 may modify the current pacing rate 560 before passing the current pacing rate 560 through to the pulse generator module 506. For instance, watchdog module 504 may adjust the current pacing rate 560 to be equal to a rest pacing rate. In some embodiments, the rest pacing rate may be equal to the base pacing rate 564. Base pacing rate 564 may be equal to an LRL of the medical device, but this is not necessary in all embodiments. In other embodiments, instead of adjusting the current pacing rate 560 to be equal to the base pacing rate 564, watchdog module 504 may adjust the current pacing rate 560 to be equal to a pacing rate 567, which is higher than base pacing rate 564 but still allows the heart to have a rest period.

Watchdog module 504 may maintain this adjustment to the current pacing rate 560 for a predetermined amount of time. In some embodiments, the predetermined amount of time may be between about fifteen minutes and about four hours and fifteen minutes, although this is just one example. In more specific embodiments, the predetermined amount of time may be about fifteen minutes, about thirty minutes, about forty-five minutes, about one hour, about one hour and fifteen minutes, about one hour and thirty minutes, about one hour and forty-five minutes, about two hours minutes, about two hours and fifteen minutes, about two hours and thirty minutes, about two hours and forty-five minutes, about three hours, about three hours and fifteen minutes, about three hours and thirty minutes, about three hours and forty-five minutes, about four hours, about four hours and fifteen minutes, or any other suitable amount of time. In some cases, the predetermined amount of time may be programmable, such as by a physician.

Figure 10:
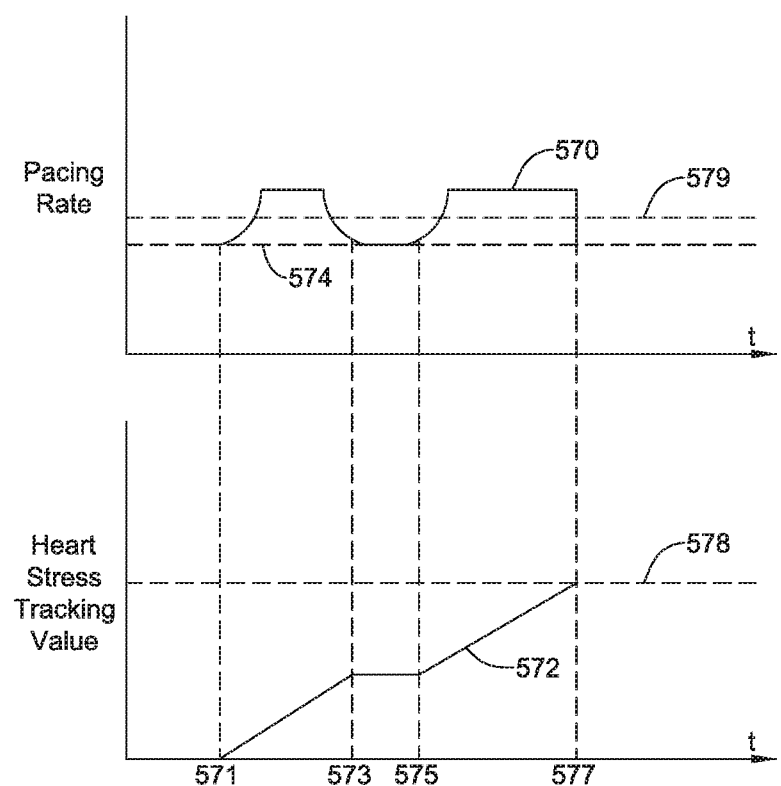
FIG. 10 depicts another graph of a current pacing rate versus time and a corresponding graph of a heart stress tracking value and how the current pacing rate may be modified based on the heart stress tracking value, in accordance with aspects of the present disclosure.

In some cases, watchdog module 504 may pause and/or reset the HSTV under certain conditions. FIG. 10 depicts one example of how watchdog module 504 may operate after the current pacing rate falls back to the base pacing rate before the HSTV has crossed the HSTV threshold. FIG. 10 depicts current pacing rate 570 versus time along with the corresponding HSTV 572. Once current pacing rate 570 rises above the base pacing rate 574, as at time 571, watchdog module 504 may begin to increment HSTV 572 at a first rate as shown. However, before HSTV 572 reaches HSTV threshold 578, current pacing rate 570 falls back to base pacing rate 574 at time 573. While current pacing rate 570 stays at or below base pacing rate 574, watchdog module 504 may not further increment HSTV 572. Instead, watchdog module 504 may begin tracking a period of time. If the period of time expires before the current pacing rate 570 again increases above base pacing rate 574, watchdog module 504 may clear or reset HSTV 572. In the example of FIG. 10, before the period of time expires, current pacing rate 570 increases above base pacing rate 574 again at time 575. Watchdog module 504 then resumes incrementing HSTV 572 as shown. Eventually, HSTV 572 reaches HSTV threshold 578 and watchdog module 504 begins a rest pacing period at time 577.

Although current pacing rate 570 is shown falling back to base pacing rate 574 before watchdog module 504 pauses incrementing HSTV 572, in other embodiments, watchdog module 504 may operate differently. For instance, watchdog module 504 may pause incrementing HSTV 572 before current pacing rate 570 falls all the way back to base pacing rate 574, such as when current pacing rate 570 falls to pacing rate 579. Further variations are contemplated by this disclosure of when and how watchdog module 504 pauses incrementing HSTV 572.

Figure 11:
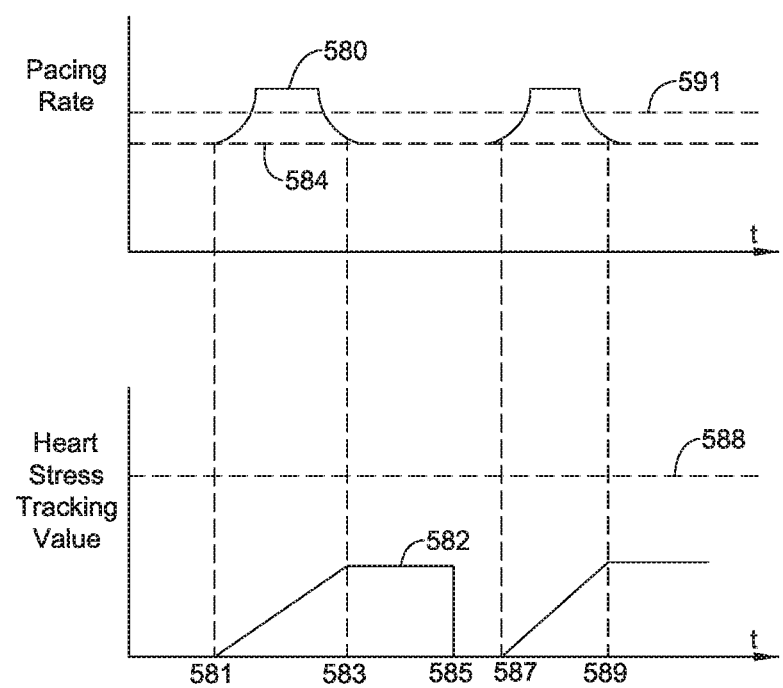
FIG. 11 depicts another graph of a current pacing rate versus time and a corresponding graph of how a heart stress tracking value may be modified based on the current pacing rate, in accordance with aspects of the present disclosure.

FIG. 11 depicts an example where watchdog module 504 resets the HSTV. FIG. 11 depicts current pacing rate 580 versus time along with the corresponding HSTV 582. As with the example of FIG. 10, when current pacing rate 580 rises above base pacing rate 584, watchdog module 504 may begin incrementing HSTV 582, as at time 581. However, once current pacing rate 580 falls back to base pacing rate 584 (or pacing rate 591) before HSTV 582 reaches HSTV threshold 588, as at time 583, watchdog module 504 pauses incrementing HSTV 582. At this point, watchdog module 504 may begin tracking a period of time. Once the period of time expires, watchdog module 504 may reset HSTV 582, such as at time 585. FIG. 11 goes on to show that, after resetting HSTV 582 at time 585, once current pacing rate 580 again rises above base pacing rate 584 at time 587, watchdog module 504 may again begin to increment HSTV 582. Further, when current pacing rate 580 falls back to base pacing rate 584 at time 589, watchdog module 504 once again pauses incrementing HSTV 582.

In some instances, the period of time that watchdog module 504 tracks before resetting the HSTV may be dependent on the value of the HSTV in relation to the HSTV threshold. For instance, the closer the HSTV is to the HSTV threshold, the longer the period of time may be that watchdog module 504 tracks before resetting the HSTV value.

In some cases, instead of pausing incrementing the HSTV when the current pacing rate falls below a threshold, watchdog module 504 may begin decrementing the HSTV. As one example, in FIG. 10, instead of pausing incrementing HSTV 572 at time 573, watchdog module 504 may begin decrementing HSTV 572 such that the graph of HSTV 572 would have a negative slope between times 573 and 575. It should be understood that a similar approach may be applied to other embodiments of the HSTV, for instance where the HSTV is decremented down from a staring value to zero as opposed to incremented up to a threshold value. In such a case, the watchdog module 504 may begin incrementing HSTV 572 when the current pacing rate falls below a threshold.

Figure 12:
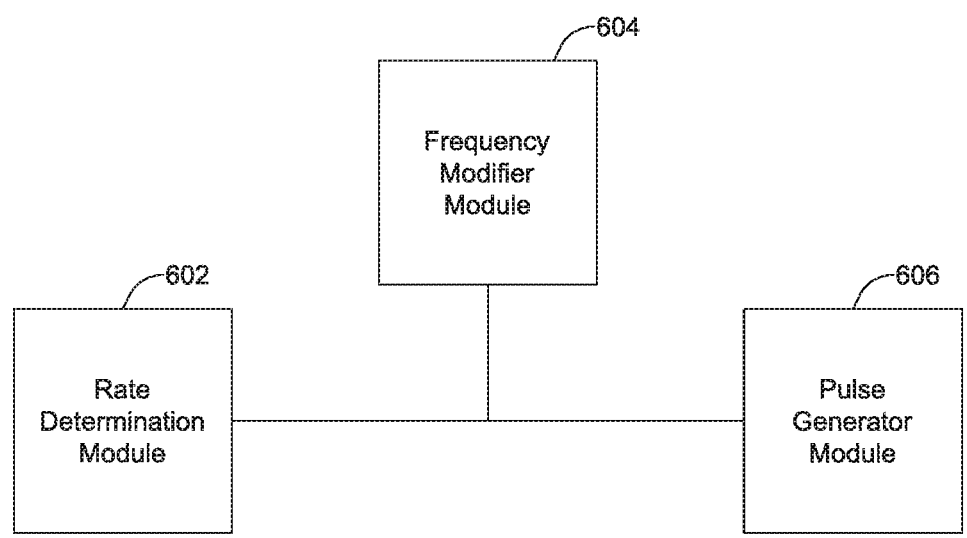
FIG. 12 depicts a block diagram of another example circuit for implementing a watchdog function, according to one aspect of the present disclosure.
Figure 13:
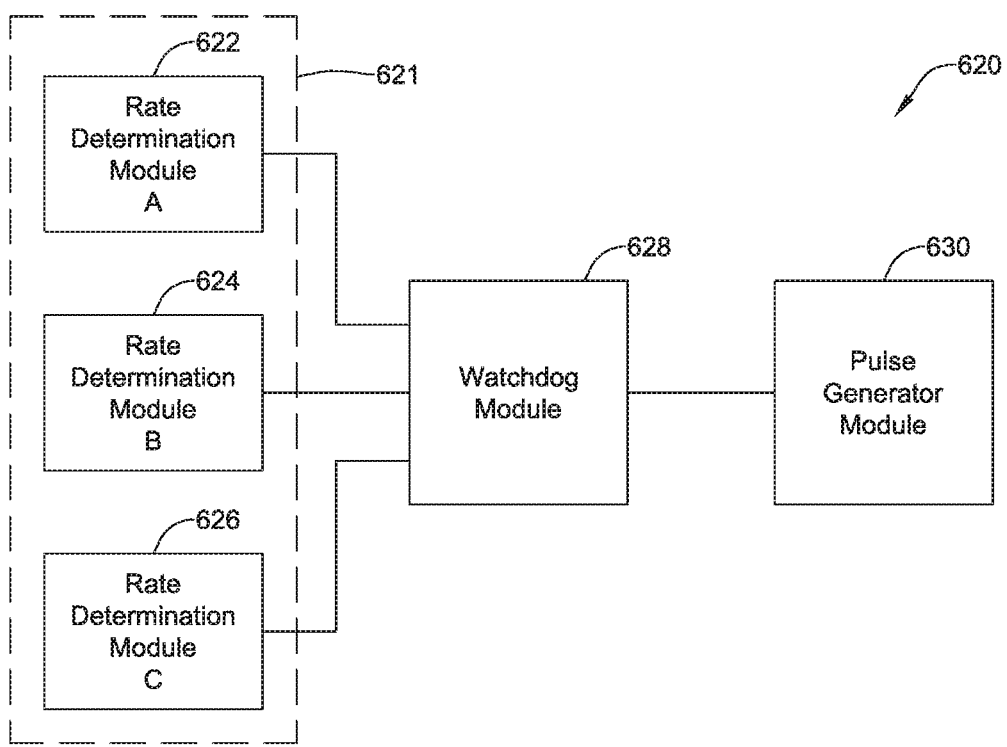
FIG. 13 depicts a block diagram of yet another example circuit for implementing a watchdog function, according to one aspect of the present disclosure.

FIGS. 12 and 13 depicts other illustrative ways in which the pacing circuit may be implemented. For instance, FIG. 12 depicts controller circuit 600 that includes a rate determination module 602, a watchdog module 604, and a pulse generator module 606. As opposed to controller circuit 500 of FIG. 5, controller circuit 600 includes watchdog module 604 connected in parallel with rate determination module 602 and pulse generator module 606. In these embodiments, instead of acting as a pass through for the current pacing rate that rate determination module 602 generates, watchdog module 604 may monitor the current pacing rate that rate determination module 602 communicates to pulse generator module 606 and may send separate control signals to the pulse generator module 606 to modify the pacing rate of pulse generator module 606, in accordance with the above disclosed techniques. Alternatively, watchdog module 604 may monitor the current pacing rate that rate determination module 602 communicates to pulse generator module 606 and may send separate control signals to the rate determination module 602 to modify the pacing rate of pulse generator module 606, in accordance with the above disclosed techniques.

In the example of FIG. 13, as illustrated at 620, the rate determination module 621, may be comprised of sub rate determination modules, such as rate determination module A 622, rate determination module B 624, and rate determination module C 626. Each of rate determination module A 622, rate determination module B 624, and rate determination module C 626 may represent a different rate drive that produces a pacing rate based on different information (e.g. using different sensor or sensor combinations to estimate the current metabolic demand). In these embodiments, watchdog module 628 may monitor the pacing rate produced by each of rate determination module A 622, rate determination module B 624, and rate determination module C 626 and may pass through the highest determined pacing rate to rate determination module 630. Watchdog module 628 may further act in accordance with the disclosed techniques to limit the amount of time pulse generator 630 spends generating pacing pulses at an elevated pacing rate.

In some cases, some or all of the different thresholds and time periods may be programmable. For instance, as described with respect to FIG. 4 a medical device implementing the disclosed techniques, such as LCP 100 or MD 200, may communicate with a device such as external support device 420. When so provided, a user (e.g. physician) may interact with external support device 420 to communicate with LCP 100 or medical device 200, such as to change one or more programmable features of LCP 100 or MD 200. Some example parameters that may be programmable include the lower rate limit (LRL), the base pacing rate, the rest pacing rate, the metabolic demand thresholds, the length of the rest pacing period, the length of the time period before resetting the HSTV, the rates at which the HSTV is incremented or decremented, or any of the other thresholds or time periods disclosed herein.

In some cases, the techniques of the present disclosure may be implemented by a system of devices. For instance, a patient may be implanted with multiple devices that may be in communication with each other, such as in the example of FIG. 4. In such cases, one of the devices, for instance pulse generator 406, may determine the current pacing rate and may communicated the current pacing rate to another other device of the system, such as LCP 402, and LCP 402 may deliver pacing pulses to the heart of the patient at the received current pacing rate. In these embodiments, either device, e.g. pulse generator 406 or LCP 402, may implement the watchdog module described herein. Where pulse generator 406 implements the watchdog module, the watchdog module may modify the current pacing rate, as described herein, before pulse generator 406 communicates the current pacing rate to LCP 402. Where LCP 402 implements the watchdog module, after receiving the current pacing rate from pulse generator 406, the watchdog module of LCP 402 may modify the current pacing rate or otherwise cause an adjustment of the rate of delivery of pacing pulses by LCP 402 in accordance with the disclosed techniques.

Additionally, as mentioned previously, in some embodiments another device may determine the pacing rate and communicate the pacing rate to LCP 100, which implements the presently disclosed watchdog techniques. However, in still other embodiments, the other device that determines the pacing rate may further implement the presently disclosed watchdog techniques. For instance, before communicating the pacing rate to LCP 100, the other device may run the determine pacing rate through the disclosed watchdog processes to produce an processed pacing rate. This processed pacing rate, which may have been modified by the watchdog processes, is then communicated to LCP 100.

Those skilled in the art will recognize that the present disclosure may be manifested in a variety of forms other than the specific embodiments described and contemplated herein. For instance, as described herein, various embodiments include one or more modules described as performing various functions. However, other embodiments may include additional modules that split the described functions up over more modules than that described herein. Additionally, other embodiments may consolidate the described functions into fewer modules.

Although various features may have been described with respect to less than all embodiments, this disclosure contemplates that those features may be included or combined with any embodiment. Further, although the embodiments described herein may have omitted some combinations of the various described features, this disclosure contemplates embodiments that include any combination of each described feature. Accordingly, departure in form and detail may be made without departing from the scope and spirit of the present disclosure as described in the appended claims.

What is claimed is:

1. A Leadless Cardiac Pacemaker (LCP) comprising:
   an outer housing;
   a plurality of exposed electrodes connected relative to the outer housing; and
   a controller disposed within the outer housing and operatively connected to the plurality of exposed electrodes, wherein the controller is configured to:

deliver pacing pulses via the plurality of exposed electrodes at a base pacing rate;

detect a measure of metabolic demand, wherein the measure of metabolic demand varies over time;

deliver pacing pulses at an elevated pacing rate relative to the base pacing rate after determining an elevated metabolic demand with respect to a base measure of metabolic demand, wherein the elevated pacing rate varies with time and is dependent on the detected measure of metabolic demand;

adjust a heart stress tracking value during times when pacing pulses are delivered at the elevated pacing rate, wherein the heart stress tracking value is adjusted faster during times when higher elevated pacing rates are delivered relative to times when lower elevated pacing rates are delivered; and determine when the heart stress tracking value crosses a predetermined heart stress threshold, and when the heart stress tracking value crosses the predetermined stress threshold, reducing the elevated pacing rate back toward the base pacing rate.

2. The LCP of claim 1, wherein the controller is configured to increase the heart stress tracking value monotonically over time.

3. The LCP of claim 1, wherein the controller is configured to decrease the heart stress tracking value monotonically over time.

4. The LCP of claim 1, wherein the controller is configured to deliver pacing pulses at the base pacing rate when the measure of metabolic demand is no longer elevated with respect to the base measure of metabolic demand.

5. The LCP of claim 1, wherein the controller is configured to reset the heart stress tracking value when the pacing pulses are no longer being delivered at the elevated pacing rate for at least a predetermined length of time.

6. The LCP of claim 1, wherein the controller is further configured to pause adjusting the heart stress tracking value when the elevated pacing rate falls below a threshold pacing rate that is higher than the base pacing rate.

7. The LCP of claim 1, further comprising an accelerometer disposed within the outer housing, and wherein the controller is configured to detect the measure of metabolic demand at least in part by monitoring an output of the accelerometer.

8. The LCP of claim 1, wherein the controller is configured to detect the measure of metabolic demand at least in part by monitoring an impedance signal via the plurality of exposed electrodes.

9. The LCP of claim 8, wherein the impedance signal provides a measure of respiration rate.

10. The LCP of claim 1, wherein the controller is configured to reduce the elevated pacing rate to the base pacing rate when the heart stress tracking value crosses the predetermined heart stress threshold.

11. The LCP of claim 10, wherein the base pacing rate is a lower rate limit.

12. The LCP of claim 10, wherein a counter is used to adjust the heart stress tracking value during times when pacing pulses are delivered at the elevated pacing rate.

13. The LCP of claim 12, wherein the counter is incremented at a faster rate during times when higher elevated pacing rates are delivered relative to times when lower elevated pacing rates are delivered.

14. A method for adjusting a pacing rate of a medical device, the method comprising:

generating, by the medical device, pacing pulses at a pacing rate that varies over time based on a determined metabolic demand;

adjusting, by the medical device, a heart stress tracking value while generating pacing pulses at or above a first pacing rate, wherein a rate of adjustment of the heart stress tracking value is dependent on a current pacing rate;

determining, by the medical device, when the heart stress tracking value crosses a predetermined heart stress threshold;

after determining that the heart stress tracking value crossed the predetermined heart stress threshold, generating, by the medical device, pacing pulses at a second pacing rate, wherein the second pacing rate is lower than the first pacing rate.

15. The method of claim 14, further comprising resetting the heart stress tracking value, by the medical device, after generating pacing pulses at pacing rates below a pacing rate threshold that is below the first pacing rate for a predetermined amount of time.

16. An implantable medical device for generating pacing pulses to a heart of a patient, the implantable medical device comprising:

a plurality of electrodes for delivering pacing pulses to the heart of the patient;

a pulse generator operatively coupled to the plurality of electrodes, the pulse generator configured to:
  generate pacing pulses at a current pacing rate;
  deliver the pacing pulses to the plurality of electrodes; and a controller operatively coupled to the pulse generator, the controller comprising:
  a pacing rate circuit configured to determine the current pacing rate for the pulse generator; and
  a watchdog circuit configured to:
    monitor the current pacing rate over time, and force the current pacing pulse of the pulse generator to be at a base pacing rate when the current pacing rate rises above a predetermined pacing rate threshold at a start time and remains above the predetermined pacing rate threshold for a predetermined threshold amount of time; and
    when the current pacing rate falls below the predetermined pacing rate threshold before the predetermined threshold amount of time expires, and remains below the predetermined pacing rate threshold for at least a threshold amount of time, reset the start time at a next time the current pacing rate again rises above the predetermined pacing rate threshold.

17. The implantable medical device of claim 16, wherein after forcing the current pacing rate of the pulse generator to be at the base pacing rate, the watchdog circuit is configured to maintain the current pacing rate at the base pacing rate for at least a predetermined rest period of time.

18. The implantable medical device of claim 16, wherein the predetermined threshold amount of time is dependent on the current pacing rate while the current pacing rate remains above the predetermined pacing rate threshold.

19. The implantable medical device of claim 16, wherein the pacing rate circuit determines the current pacing rate in a rate responsive manner.

20. The implantable medical device of claim 16, wherein the implantable medical device is a leadless cardiac pacemaker configured to be implanted on or within a heart.

* * * * *